US012653944B2

(12) United States Patent　　　　(10) Patent No.: US 12,653,944 B2

Marsh et al.　　　　　　　　　　　　(45) Date of Patent: Jun. 16, 2026

(54) SYSTEM AND METHOD HAVING TRANSITION PHASE IN MULTI-PHASE INJECTION PROTOCOL

(71) Applicant: BAYER HEALTHCARE LLC, Whippany, NJ (US)

(72) Inventors: Chelsea Marsh, Pittsburgh, PA (US); William Barone, Pittsburgh, PA (US); Michael Spohn, Fenelton, PA (US); Kevin Fleischmann, Bethel Park, PA (US); Michael Mcdermott, Pittsburgh, PA (US)

(73) Assignee: BAYER HEALTHCARE LLC, Whippany, NJ (US)

( * ) Notice: Subject to any disclaimer, the term of this patent is extended or adjusted under 35 U.S.C. 154(b) by 484 days.

(21) Appl. No.: 16/621,777

(22) PCT Filed: Aug. 28, 2018

(86) PCT No.: PCT/US2018/048282

§ 371 (c)(1),
(2) Date: Dec. 12, 2019

(87) PCT Pub. No.: WO2019/046259

PCT Pub. Date: Mar. 7, 2019

(65) Prior Publication Data

US 2020/0206414 A1　　Jul. 2, 2020

Related U.S. Application Data

(60) Provisional application No. 62/552,494, filed on Aug. 31, 2017.

(51) Int. Cl.
*A61M 5/14*　　　　(2006.01)
*A61M 5/00*　　　　(2006.01)
(Continued)

(52) U.S. Cl.
CPC .......... *A61M 5/1408* (2013.01); *A61M 5/007* (2013.01); *A61M 5/1422* (2013.01); *A61M 5/16827* (2013.01); *A61M 2205/3334* (2013.01)

(58) Field of Classification Search
CPC .. A61M 5/1408; A61M 5/007; A61M 5/1422; A61M 5/16827;
(Continued)

(56) References Cited

U.S. PATENT DOCUMENTS

| 383,858 A | 6/1888 | Campbell |
| 508,584 A | 11/1893 | Stevens |

(Continued)

FOREIGN PATENT DOCUMENTS

| CA | 2045070 A1 | 2/1992 |
| CA | 2077712 A1 | 12/1993 |

(Continued)

OTHER PUBLICATIONS

Angelini, P., "Use of mechanical injectors during percutaneous transluminal coronary angioplasty (PTCA)," Catheterization and Cardiovascular Diagnosis, vol. 16, Issue 3, pp. 193-194, Mar. 1989.

(Continued)

*Primary Examiner* — Kami A Bosworth
*Assistant Examiner* — Avery Smale
(74) *Attorney, Agent, or Firm* — Joseph L. Kent; James R. Stevenson

(57)　　　　　　　ABSTRACT

A method of delivering a multi-phase fluid injection to a patient via a fluid injector comprising two or more syringes includes injecting a first fluid of the fluid injection from at least a first syringe at a first predetermined flow rate, wherein the first fluid has a first viscosity; injecting an initial portion of a second fluid from at least a second syringe at an intermediate flow rate different than a second predetermined (Continued)

flow rate for a specified time, the second fluid having a second viscosity different from the first viscosity; and injecting a remaining portion of the second fluid of the fluid injection at a flow rate at the second predetermined flow rate. A fluid injector system configured for delivering a multiphase fluid injection is disclosed.

7 Claims, 15 Drawing Sheets

(51) Int. Cl.
  *A61M 5/142* (2006.01)
  *A61M 5/168* (2006.01)
(58) Field of Classification Search
  CPC ........... A61M 2005/14553; A61M 2205/3334;
      A61M 5/1407; A61M 2005/1402; A61M
      2005/1403; A61M 2005/1787; A61M
      5/1409; A61M 2005/14208; A61M 5/172;
      A61M 5/16877; A61M 5/168; A61M
      5/16804; A61M 2205/3331
  See application file for complete search history.

(56) References Cited

U.S. PATENT DOCUMENTS

| | | | |
|---|---|---|---|
| 945,143 | A | 1/1910 | Iacques |
| 2,511,291 | A | 6/1950 | Mueller |
| 2,583,206 | A | 1/1952 | Borck et al. |
| 3,156,236 | A | 11/1964 | Williamson |
| 3,159,312 | A | 12/1964 | Van Sciver, II |
| 3,276,472 | A | 10/1966 | Jinkens et al. |
| 3,349,713 | A | 10/1967 | Fassbender |
| 3,520,295 | A | 7/1970 | Paul |
| 3,523,523 | A | 8/1970 | Heinrich et al. |
| 3,623,474 | A | 11/1971 | Heilman |
| 3,635,444 | A | 1/1972 | Potter |
| 3,671,208 | A | 6/1972 | Wayne |
| 3,701,345 | A | 10/1972 | Heilman |
| 3,719,207 | A | 3/1973 | Takeda |
| 3,755,655 | A | 8/1973 | Senecal |
| 3,769,976 | A | 11/1973 | Victory |
| 3,793,600 | A | 2/1974 | Grosbard |
| 3,812,843 | A | 5/1974 | Wootten et al. |
| 3,817,843 | A | 6/1974 | Barrett |
| 3,839,708 | A | 10/1974 | Lyons et al. |
| 3,868,967 | A | 3/1975 | Harding |
| 3,888,239 | A | 6/1975 | Rubinstein |
| 3,895,220 | A | 7/1975 | Nelson et al. |
| 3,898,983 | A | 8/1975 | Elam |
| 3,927,955 | A | 12/1975 | Spinosa et al. |
| 3,941,126 | A | 3/1976 | Dietrich et al. |
| 3,958,103 | A | 5/1976 | Oka et al. |
| 3,968,195 | A | 7/1976 | Bishop |
| 3,995,381 | A | 12/1976 | Manfred et al. |
| 4,001,549 | A | 1/1977 | Corwin |
| 4,006,736 | A | 2/1977 | Kranys et al. |
| 4,038,981 | A | 8/1977 | Lefevre et al. |
| 4,044,757 | A | 8/1977 | Mcwhorter et al. |
| 4,090,502 | A | 5/1978 | Tajika |
| 4,135,247 | A | 1/1979 | Gordon et al. |
| 4,151,845 | A | 5/1979 | Clemens |
| 4,187,057 | A | 2/1980 | Xanthopoulos |
| 4,191,183 | A | 3/1980 | Mendelson |
| 4,199,000 | A | 4/1980 | Edstrom |
| 4,204,775 | A | 5/1980 | Speer |
| 4,207,871 | A | 6/1980 | Jenkins |
| 4,208,136 | A | 6/1980 | King et al. |
| 4,223,675 | A | 9/1980 | Williams |
| 4,262,824 | A | 4/1981 | Hrynewycz |
| 4,263,916 | A | 4/1981 | Brooks et al. |
| 4,280,494 | A | 7/1981 | Cosgrove, Jr. et al. |
| 4,284,073 | A | 8/1981 | Krause et al. |
| 4,315,247 | A | 2/1982 | Germanton |
| 4,319,568 | A | 3/1982 | Tregoning |
| 4,329,067 | A | 5/1982 | Goudy, Jr. |
| 4,340,153 | A | 7/1982 | Spivey |
| 4,341,153 | A | 7/1982 | Bowser |
| 4,392,847 | A | 7/1983 | Whitney et al. |
| 4,392,849 | A | 7/1983 | Petre et al. |
| 4,396,385 | A | 8/1983 | Kelly et al. |
| 4,402,310 | A | 9/1983 | Kimura |
| 4,409,966 | A | 10/1983 | Lambrecht et al. |
| 4,434,820 | A | 3/1984 | Glass |
| 4,434,822 | A | 3/1984 | Bellamy et al. |
| 4,441,823 | A | 4/1984 | Power et al. |
| 4,444,198 | A | 4/1984 | Petre |
| 4,447,230 | A | 5/1984 | Gula et al. |
| 4,448,200 | A | 5/1984 | Brooks et al. |
| 4,474,476 | A | 10/1984 | Thomsen |
| 4,477,923 | A | 10/1984 | Baumann et al. |
| 4,479,760 | A | 10/1984 | Bilstad et al. |
| 4,479,761 | A | 10/1984 | Bilstad et al. |
| 4,479,762 | A | 10/1984 | Bilstad et al. |
| 4,504,908 | A | 3/1985 | Riederer et al. |
| 4,509,526 | A | 4/1985 | Barnes et al. |
| 4,512,764 | A | 4/1985 | Wunsch |
| 4,542,459 | A | 9/1985 | Riederer |
| 4,544,949 | A | 10/1985 | Kurihara |
| 4,551,133 | A | 11/1985 | Zegers et al. |
| 4,552,130 | A | 11/1985 | Kinoshita |
| 4,559,036 | A | 12/1985 | Wunsch |
| 4,563,175 | A | 1/1986 | Lafond |
| 4,578,802 | A | 3/1986 | Itoh |
| 4,585,009 | A | 4/1986 | Barker et al. |
| 4,585,941 | A | 4/1986 | Bergner |
| 4,610,665 | A | 9/1986 | Matsumoto et al. |
| 4,610,670 | A | 9/1986 | Spencer |
| 4,610,790 | A | 9/1986 | Reti et al. |
| 4,611,340 | A | 9/1986 | Okazaki |
| 4,612,572 | A | 9/1986 | Komatsu et al. |
| 4,625,494 | A | 12/1986 | Watschenko et al. |
| 4,626,144 | A | 12/1986 | Berner |
| 4,633,307 | A | 12/1986 | Honda |
| 4,634,426 | A | 1/1987 | Kamen |
| 4,636,144 | A | 1/1987 | Abe et al. |
| 4,655,197 | A | 4/1987 | Atkinson |
| 4,662,906 | A | 5/1987 | Matkovich et al. |
| 4,672,651 | A | 6/1987 | Horiba et al. |
| 4,676,776 | A | 6/1987 | Howson |
| 4,682,170 | A | 7/1987 | Kubota et al. |
| 4,689,670 | A | 8/1987 | Okazaki |
| 4,710,166 | A | 12/1987 | Thompson et al. |
| 4,723,261 | A | 2/1988 | Janssen et al. |
| 4,750,643 | A | 6/1988 | Wortrich |
| 4,754,786 | A | 7/1988 | Roberts |
| 4,781,687 | A | 11/1988 | Wall |
| 4,783,273 | A | 11/1988 | Knutsson et al. |
| 4,789,014 | A | 12/1988 | Digianfilippo et al. |
| 4,793,357 | A | 12/1988 | Lindstrom |
| 4,795,429 | A | 1/1989 | Feldstein |
| 4,798,590 | A | 1/1989 | O'Leary et al. |
| 4,804,454 | A | 2/1989 | Asakura et al. |
| 4,823,833 | A | 4/1989 | Hogan et al. |
| 4,835,521 | A | 5/1989 | Andrejasich et al. |
| 4,836,187 | A | 6/1989 | Iwakoshi et al. |
| 4,838,856 | A | 6/1989 | Mulreany et al. |
| 4,840,620 | A | 6/1989 | Kobayashi et al. |
| 4,844,052 | A | 7/1989 | Iwakoshi et al. |
| 4,853,521 | A | 8/1989 | Claeys et al. |
| 4,854,301 | A | 8/1989 | Nakajima |
| 4,854,324 | A | 8/1989 | Hirschman et al. |
| 4,857,056 | A | 8/1989 | Talonn |
| 4,874,359 | A | 10/1989 | White et al. |
| 4,879,880 | A | 11/1989 | Harrison |
| 4,880,014 | A | 11/1989 | Zarowitz et al. |
| 4,887,208 | A | 12/1989 | Schneider et al. |
| 4,887,554 | A | 12/1989 | Whitford |
| 4,901,731 | A | 2/1990 | Millar |
| 4,903,705 | A | 2/1990 | Imamura et al. |
| 4,913,154 | A | 4/1990 | Ermert et al. |
| 4,922,916 | A | 5/1990 | Ermert et al. |

(56)                References Cited

U.S. PATENT DOCUMENTS

| | | | |
|---|---|---|---|
| 4,925,444 A | 5/1990 | Orkin et al. |
| 4,929,818 A | 5/1990 | Bradbury et al. |
| 4,935,005 A | 6/1990 | Haines |
| 4,936,832 A | 6/1990 | Vaillancourt |
| 4,943,279 A | 7/1990 | Samiotes et al. |
| 4,943,779 A | 7/1990 | Pedersen et al. |
| 4,943,987 A | 7/1990 | Asahina et al. |
| 4,946,256 A | 8/1990 | Woodruff |
| 4,946,439 A | 8/1990 | Eggers |
| 4,947,412 A | 8/1990 | Mattson |
| 4,950,245 A | 8/1990 | Brown et al. |
| 4,952,068 A | 8/1990 | Flint |
| 4,954,129 A | 9/1990 | Giuliani et al. |
| 4,965,726 A | 10/1990 | Heuscher et al. |
| 4,966,579 A | 10/1990 | Polaschegg |
| 4,976,687 A | 12/1990 | Martin |
| 4,978,335 A | 12/1990 | Arthur, III |
| 4,981,467 A | 1/1991 | Bobo, Jr. et al. |
| 4,995,064 A | 2/1991 | Wilson et al. |
| 5,002,055 A | 3/1991 | Merki et al. |
| 5,004,472 A | 4/1991 | Wallace et al. |
| 5,009,654 A | 4/1991 | Minshall et al. |
| 5,010,473 A | 4/1991 | Jacobs |
| 5,013,173 A | 5/1991 | Shiraishi |
| 5,018,173 A | 5/1991 | Komai et al. |
| 5,026,348 A | 6/1991 | Venegas |
| 5,032,112 A | 7/1991 | Fairchild et al. |
| 5,034,987 A | 7/1991 | Fujimoto et al. |
| 5,040,537 A | 8/1991 | Katakura |
| 5,053,002 A | 10/1991 | Barlow |
| 5,054,044 A | 10/1991 | Audon et al. |
| 5,056,568 A | 10/1991 | Digianfilippo et al. |
| 5,059,171 A | 10/1991 | Bridge et al. |
| 5,059,173 A | 10/1991 | Sacco |
| 5,061,243 A | 10/1991 | Winchell et al. |
| 5,069,662 A | 12/1991 | Bodden |
| 5,078,683 A | 1/1992 | Sancoff et al. |
| 5,088,981 A | 2/1992 | Howson et al. |
| 5,100,380 A | 3/1992 | Epstein et al. |
| 5,104,374 A | 4/1992 | Bishko et al. |
| 5,104,387 A | 4/1992 | Pokorney et al. |
| 5,108,365 A | 4/1992 | Woods, Jr. |
| 5,111,492 A | 5/1992 | Klausz |
| 5,113,905 A | 5/1992 | Pruitt et al. |
| 5,123,056 A | 6/1992 | Wilson |
| 5,123,121 A | 6/1992 | Broersma |
| 5,125,018 A | 6/1992 | Asahina |
| 5,128,121 A | 7/1992 | Berg et al. |
| 5,133,336 A | 7/1992 | Savitt et al. |
| 5,135,000 A | 8/1992 | Akselrod et al. |
| 5,140,862 A | 8/1992 | Pappalardo |
| 5,150,292 A | 9/1992 | Hoffmann et al. |
| 5,163,928 A | 11/1992 | Hobbs et al. |
| 5,166,961 A | 11/1992 | Brunnett et al. |
| 5,180,895 A | 1/1993 | Briggs et al. |
| 5,180,896 A | 1/1993 | Gibby et al. |
| 5,190,744 A | 3/1993 | Rocklage et al. |
| 5,191,878 A | 3/1993 | Iida et al. |
| 5,196,007 A | 3/1993 | Ellman et al. |
| 5,199,604 A | 4/1993 | Palmer et al. |
| 5,207,642 A | 5/1993 | Orkin et al. |
| 5,215,095 A | 6/1993 | Macvicar et al. |
| 5,228,070 A | 7/1993 | Mattson |
| 5,230,614 A | 7/1993 | Zanger et al. |
| 5,242,390 A | 9/1993 | Goldrath |
| 5,249,122 A | 9/1993 | Stritzke |
| 5,249,579 A | 10/1993 | Hobbs et al. |
| 5,262,946 A | 11/1993 | Heuscher |
| 5,267,174 A | 11/1993 | Kaufman et al. |
| 5,269,756 A | 12/1993 | Dryden |
| 5,273,537 A | 12/1993 | Haskvitz et al. |
| 5,274,218 A | 12/1993 | Urata et al. |
| 5,276,614 A | 1/1994 | Heuscher |
| 5,286,252 A | 2/1994 | Tuttle et al. |
| 5,287,273 A | 2/1994 | Kupfer et al. |
| 5,295,967 A | 3/1994 | Rondelet et al. |
| 5,300,031 A | 4/1994 | Neer et al. |
| 5,301,656 A | 4/1994 | Negoro et al. |
| 5,301,672 A | 4/1994 | Kalender |
| 5,304,126 A | 4/1994 | Epstein et al. |
| 5,310,997 A | 5/1994 | Roach et al. |
| 5,311,568 A | 5/1994 | Mckee, Jr. et al. |
| 5,313,992 A | 5/1994 | Grabenkort |
| 5,317,506 A | 5/1994 | Coutre et al. |
| 5,328,463 A | 7/1994 | Barton et al. |
| 5,329,459 A | 7/1994 | Kaufman et al. |
| 5,334,141 A | 8/1994 | Carr et al. |
| 5,339,799 A | 8/1994 | Kami et al. |
| 5,349,625 A | 9/1994 | Born et al. |
| 5,349,635 A | 9/1994 | Scott |
| 5,352,979 A | 10/1994 | Conturo |
| 5,354,273 A | 10/1994 | Hagen |
| 5,361,761 A | 11/1994 | Van Lysel et al. |
| 5,362,948 A | 11/1994 | Morimoto |
| 5,368,562 A | 11/1994 | Blomquist et al. |
| 5,368,567 A | 11/1994 | Lee |
| 5,368,570 A | 11/1994 | Thompson et al. |
| 5,373,231 A | 12/1994 | Boll et al. |
| 5,376,070 A | 12/1994 | Purvis et al. |
| 5,378,231 A | 1/1995 | Johnson et al. |
| 5,382,232 A | 1/1995 | Hague et al. |
| 5,383,231 A | 1/1995 | Yamagishi |
| 5,383,858 A | 1/1995 | Reilly et al. |
| 5,385,540 A | 1/1995 | Abbott et al. |
| 5,388,139 A | 2/1995 | Beland |
| 5,392,849 A | 2/1995 | Matsunaga et al. |
| 5,400,792 A | 3/1995 | Hoebel et al. |
| 5,417,213 A | 5/1995 | Prince |
| 5,425,716 A | 6/1995 | Kawasaki et al. |
| 5,431,627 A | 7/1995 | Pastrone et al. |
| 5,433,704 A | 7/1995 | Ross et al. |
| 5,445,621 A | 8/1995 | Poli et al. |
| 5,450,847 A | 9/1995 | Kaempfe et al. |
| 5,453,639 A | 9/1995 | Cronin et al. |
| 5,456,255 A | 10/1995 | Abe et al. |
| 5,458,128 A | 10/1995 | Polanyi et al. |
| 5,459,769 A | 10/1995 | Brown |
| 5,460,609 A | 10/1995 | O'Donnell |
| 5,464,391 A | 11/1995 | Devale |
| 5,468,240 A | 11/1995 | Gentelia et al. |
| 5,469,769 A | 11/1995 | Sawada et al. |
| 5,469,849 A | 11/1995 | Sasaki et al. |
| 5,472,403 A | 12/1995 | Cornacchia et al. |
| 5,474,683 A | 12/1995 | Bryant et al. |
| 5,485,831 A | 1/1996 | Holdsworth et al. |
| 5,489,265 A | 2/1996 | Montalvo et al. |
| 5,494,036 A | 2/1996 | Uber, III et al. |
| 5,494,822 A | 2/1996 | Sadri |
| 5,496,273 A | 3/1996 | Pastrone et al. |
| 5,507,412 A | 4/1996 | Ebert et al. |
| 5,515,851 A | 5/1996 | Goldstein |
| 5,522,798 A | 6/1996 | Johnson et al. |
| 5,531,679 A | 7/1996 | Schulman et al. |
| 5,531,697 A | 7/1996 | Olsen et al. |
| 5,533,978 A | 7/1996 | Teirstein |
| 5,544,215 A | 8/1996 | Shroy, Jr. et al. |
| 5,547,470 A | 8/1996 | Johnson et al. |
| 5,552,130 A | 9/1996 | Kraus et al. |
| 5,553,619 A | 9/1996 | Prince |
| 5,560,317 A | 10/1996 | Bunyan et al. |
| 5,566,092 A | 10/1996 | Wang et al. |
| 5,569,181 A | 10/1996 | Heilman et al. |
| 5,569,208 A | 10/1996 | Woelpper et al. |
| 5,573,515 A | 11/1996 | Wilson et al. |
| 5,579,767 A | 12/1996 | Prince |
| 5,583,902 A | 12/1996 | Bae |
| 5,590,654 A | 1/1997 | Prince |
| 5,592,940 A | 1/1997 | Kampfe et al. |
| 5,601,086 A | 2/1997 | Pretlow, III et al. |
| 5,611,344 A | 3/1997 | Bernstein et al. |
| 5,616,124 A | 4/1997 | Hague et al. |
| 5,651,776 A | 7/1997 | Appling et al. |
| 5,681,285 A | 10/1997 | Ford et al. |
| 5,687,208 A | 11/1997 | Bae et al. |

(56) References Cited

U.S. PATENT DOCUMENTS

| | | | |
|---|---|---|---|
| 5,687,708 A | 11/1997 | Farnsworth et al. |
| 5,713,358 A | 2/1998 | Mistretta et al. |
| 5,724,976 A | 3/1998 | Mine et al. |
| 5,725,500 A | 3/1998 | Micheler |
| 5,739,508 A | 4/1998 | Uber, III |
| 5,743,266 A | 4/1998 | Levene et al. |
| 5,768,405 A | 6/1998 | Makram-Ebeid |
| 5,796,862 A | 8/1998 | Pawlicki et al. |
| 5,799,649 A | 9/1998 | Prince |
| 5,800,397 A | 9/1998 | Wilson et al. |
| 5,806,519 A | 9/1998 | Evans, III et al. |
| 5,808,203 A | 9/1998 | Nolan, Jr. et al. |
| 5,827,219 A | 10/1998 | Uber, III et al. |
| 5,827,504 A | 10/1998 | Yan et al. |
| 5,840,026 A | 11/1998 | Uber, III et al. |
| 5,843,037 A | 12/1998 | Uber, III |
| 5,846,517 A | 12/1998 | Unger |
| 5,865,744 A | 2/1999 | Lemelson |
| 5,873,861 A | 2/1999 | Hitchins et al. |
| 5,881,124 A | 3/1999 | Giger et al. |
| 5,882,343 A | 3/1999 | Wilson et al. |
| 5,902,054 A | 5/1999 | Coudray |
| 5,903,454 A | 5/1999 | Hoffberg et al. |
| 5,916,165 A | 6/1999 | Duchon et al. |
| 5,920,054 A | 7/1999 | Uber, III |
| 5,947,935 A | 9/1999 | Kazousky et al. |
| 5,954,668 A | 9/1999 | Uber, III et al. |
| 5,964,703 A | 10/1999 | Goodman et al. |
| 5,987,347 A | 11/1999 | Khoury et al. |
| 5,988,587 A | 11/1999 | Duchon et al. |
| 6,046,225 A | 4/2000 | Maddock |
| 6,055,985 A | 5/2000 | Bae et al. |
| 6,056,902 A | 5/2000 | Hettinga |
| 6,063,052 A | 5/2000 | Uber, III et al. |
| 6,073,042 A | 6/2000 | Simonetti |
| 6,099,502 A | 8/2000 | Duchon et al. |
| 6,113,568 A | 9/2000 | Olaussen |
| 6,132,396 A | 10/2000 | Antanavich et al. |
| 6,149,627 A | 11/2000 | Uber, III |
| 6,159,183 A | 12/2000 | Neer et al. |
| 6,186,146 B1 | 2/2001 | Glickman |
| 6,201,889 B1 | 3/2001 | Vannah |
| 6,221,045 B1 | 4/2001 | Duchon et al. |
| 6,236,706 B1 | 5/2001 | Hsieh |
| 6,248,093 B1 | 6/2001 | Moberg |
| 6,306,117 B1 | 10/2001 | Uber, III |
| 6,313,131 B1 | 11/2001 | Lawyer |
| 6,317,623 B1 | 11/2001 | Griffiths et al. |
| 6,322,535 B1 | 11/2001 | Hitchins et al. |
| 6,344,030 B1 | 2/2002 | Duchon et al. |
| 6,375,624 B1 | 4/2002 | Uber, III et al. |
| 6,381,486 B1 | 4/2002 | Mistretta et al. |
| 6,387,098 B1 | 5/2002 | Cole et al. |
| 6,397,093 B1 | 5/2002 | Aldrich |
| 6,397,097 B1 | 5/2002 | Requardt |
| 6,402,697 B1 | 6/2002 | Calkins et al. |
| 6,408,204 B1 | 6/2002 | Hirschman |
| 6,423,719 B1 | 7/2002 | Lawyer |
| 6,442,418 B1 | 8/2002 | Evans, III et al. |
| 6,459,931 B1 | 10/2002 | Hirschman |
| 6,470,889 B1 | 10/2002 | Bae et al. |
| 6,471,674 B1 | 10/2002 | Emig et al. |
| 6,478,735 B1 | 11/2002 | Pope et al. |
| 6,503,226 B1 | 1/2003 | Martinell et al. |
| 6,520,930 B2 | 2/2003 | Critchlow et al. |
| 6,527,718 B1 | 3/2003 | Connor et al. |
| 6,554,819 B2 | 4/2003 | Reich |
| 6,556,695 B1 | 4/2003 | Packer et al. |
| 6,572,851 B2 | 6/2003 | Muramatsu et al. |
| 6,574,496 B1 | 6/2003 | Golman et al. |
| 6,575,930 B1 | 6/2003 | Trombley, III et al. |
| 6,597,938 B2 | 7/2003 | Liu |
| 6,626,862 B1 | 9/2003 | Duchon et al. |
| 6,635,030 B1 | 10/2003 | Bae et al. |
| 6,643,537 B1 | 11/2003 | Zatezalo et al. |
| 6,652,489 B2 | 11/2003 | Trocki et al. |
| 6,656,157 B1 | 12/2003 | Duchon et al. |
| 6,673,033 B1 | 1/2004 | Sciulli et al. |
| 6,685,733 B1 | 2/2004 | Dae et al. |
| 6,691,047 B1 | 2/2004 | Fredericks |
| 6,699,219 B2 | 3/2004 | Emig et al. |
| 6,731,971 B2 | 5/2004 | Evans et al. |
| 6,751,500 B2 | 6/2004 | Hirschman |
| 6,754,521 B2 | 6/2004 | Prince |
| 6,775,764 B1 | 8/2004 | Batcher |
| 6,776,764 B2 | 8/2004 | Pinsky |
| 6,866,653 B2 | 3/2005 | Bae |
| 6,876,720 B2 | 4/2005 | Tsuyuki |
| 6,879,853 B2 | 4/2005 | Meaney et al. |
| 6,983,590 B2 | 1/2006 | Roelle et al. |
| 7,047,058 B1 | 5/2006 | Dvorsky et al. |
| 7,094,216 B2 | 8/2006 | Trombley, III et al. |
| 7,122,012 B2 | 10/2006 | Bouton et al. |
| 7,267,666 B1 | 9/2007 | Duchon et al. |
| 7,267,667 B2 | 9/2007 | Houde et al. |
| 7,292,720 B2 | 11/2007 | Horger et al. |
| 7,351,221 B2 | 4/2008 | Trombley et al. |
| 7,553,294 B2 | 6/2009 | Lazzaro et al. |
| 7,553,295 B2 | 6/2009 | Susi |
| 7,556,619 B2 | 7/2009 | Spohn et al. |
| 7,563,249 B2 | 7/2009 | Schriver et al. |
| 7,591,792 B2 | 9/2009 | Bouton |
| 7,666,169 B2 | 2/2010 | Cowan et al. |
| 7,688,057 B2 | 3/2010 | Foss et al. |
| 7,861,893 B2 | 1/2011 | Voegele et al. |
| 7,925,330 B2 | 4/2011 | Kalafut et al. |
| 7,937,134 B2 | 5/2011 | Uber et al. |
| 8,007,487 B2 | 8/2011 | Patrick et al. |
| 8,057,406 B2 | 11/2011 | Mohiuddin |
| 8,147,464 B2 | 4/2012 | Spohn et al. |
| 8,162,903 B2 | 4/2012 | Reilly et al. |
| 8,235,949 B2 | 8/2012 | Hack et al. |
| 8,295,914 B2 | 10/2012 | Kalafut et al. |
| 8,295,920 B2 | 10/2012 | Bouton et al. |
| 8,337,456 B2 | 12/2012 | Schriver et al. |
| 8,377,003 B2 | 2/2013 | Wagner |
| 8,403,909 B2 | 3/2013 | Spohn et al. |
| 8,439,863 B2 | 5/2013 | Fago et al. |
| 8,486,017 B2 | 7/2013 | Masuda et al. |
| 8,905,969 B2 | 12/2014 | Nystrom et al. |
| 8,945,051 B2 | 2/2015 | Schriver et al. |
| 9,101,708 B2 | 8/2015 | Small et al. |
| 9,173,995 B1 | 11/2015 | Tucker et al. |
| 9,199,033 B1 | 12/2015 | Cowan et al. |
| 9,238,099 B2 | 1/2016 | Kalafut et al. |
| 9,242,083 B2 | 1/2016 | Fago et al. |
| 9,259,527 B2 | 2/2016 | Spohn et al. |
| 9,289,550 B1 | 3/2016 | Dvorsky et al. |
| 9,314,749 B2 | 4/2016 | Yagi et al. |
| 9,326,686 B2 | 5/2016 | Warren et al. |
| 9,333,293 B2 | 5/2016 | Williams, Jr. et al. |
| 9,474,857 B2 | 10/2016 | Riley et al. |
| 9,480,788 B2 | 11/2016 | Wagner |
| 9,480,791 B2 | 11/2016 | Reilly |
| 9,555,379 B2 | 1/2017 | Schriver et al. |
| 9,566,381 B2 | 2/2017 | Barron et al. |
| 9,861,752 B2 | 1/2018 | Buder et al. |
| 9,901,671 B2 | 2/2018 | Toews et al. |
| 9,987,413 B2 | 6/2018 | Seibold et al. |
| 10,041,483 B2 | 8/2018 | Chappel et al. |
| 10,112,008 B2 | 10/2018 | Neftel et al. |
| 10,124,110 B2 | 11/2018 | Dedig et al. |
| 10,201,666 B2 | 2/2019 | Cowan et al. |
| D847,985 S | 5/2019 | Neff et al. |
| 10,391,234 B2 | 8/2019 | Sams et al. |
| 10,398,353 B2 | 9/2019 | Addison et al. |
| 10,507,319 B2 | 12/2019 | Haury et al. |
| 10,549,084 B2 | 2/2020 | Sokolov et al. |
| 10,583,256 B2 | 3/2020 | Berry et al. |
| 10,933,190 B2 | 3/2021 | Berry et al. |
| 11,141,535 B2 | 10/2021 | Uber, III et al. |
| 11,478,581 B2 | 10/2022 | Mcdermott et al. |
| 2001/0018937 A1 | 9/2001 | Nemoto |
| 2001/0027265 A1 | 10/2001 | Prince |

(56) References Cited

U.S. PATENT DOCUMENTS

| | | | |
|---|---|---|---|
| 2001/0056233 A1 | 12/2001 | Uber et al. | |
| 2002/0007116 A1* | 1/2002 | Zatezalo | A61M 5/172 |
| | | | 604/152 |
| 2002/0010551 A1 | 1/2002 | Wang et al. | |
| 2002/0026148 A1 | 2/2002 | Uber et al. | |
| 2002/0099254 A1 | 7/2002 | Movahed | |
| 2002/0123702 A1 | 9/2002 | Cho | |
| 2002/0151854 A1 | 10/2002 | Duchon et al. | |
| 2003/0050556 A1 | 3/2003 | Uber et al. | |
| 2003/0120171 A1 | 6/2003 | Diamantopoulos et al. | |
| 2003/0195462 A1 | 10/2003 | Mann et al. | |
| 2003/0212364 A1 | 11/2003 | Mann et al. | |
| 2003/0216683 A1 | 11/2003 | Shekalim | |
| 2003/0226539 A1 | 12/2003 | Kim et al. | |
| 2004/0011740 A1 | 1/2004 | Bernard et al. | |
| 2004/0025452 A1 | 2/2004 | Mclean | |
| 2004/0044302 A1 | 3/2004 | Bernard et al. | |
| 2004/0064041 A1 | 4/2004 | Lazzaro et al. | |
| 2004/0092905 A1 | 5/2004 | Azzolini | |
| 2004/0097806 A1 | 5/2004 | Hunter et al. | |
| 2004/0154788 A1 | 8/2004 | Symonds | |
| 2004/0162484 A1 | 8/2004 | Nemoto | |
| 2004/0163655 A1 | 8/2004 | Gelfand et al. | |
| 2004/0167415 A1 | 8/2004 | Gelfand et al. | |
| 2004/0171923 A1 | 9/2004 | Kalafut et al. | |
| 2004/0199076 A1* | 10/2004 | Nemoto | A61M 5/14546 |
| | | | 600/432 |
| 2004/0215144 A1 | 10/2004 | Duchon et al. | |
| 2004/0253183 A1 | 12/2004 | Uber, III et al. | |
| 2004/0254533 A1 | 12/2004 | Schriver et al. | |
| 2005/0025630 A1 | 2/2005 | Ayre et al. | |
| 2005/0107697 A1 | 5/2005 | Berke et al. | |
| 2005/0171487 A1 | 8/2005 | Haury et al. | |
| 2005/0234407 A1 | 10/2005 | Spohn et al. | |
| 2005/0234428 A1 | 10/2005 | Spohn et al. | |
| 2006/0052794 A1 | 3/2006 | Mcgill et al. | |
| 2006/0079765 A1 | 4/2006 | Neer et al. | |
| 2006/0079843 A1 | 4/2006 | Brooks et al. | |
| 2006/0135940 A1 | 6/2006 | Joshi | |
| 2006/0167415 A1 | 7/2006 | Nemoto | |
| 2006/0173360 A1 | 8/2006 | Kalafut et al. | |
| 2006/0211970 A1 | 9/2006 | Sciulli | |
| 2007/0068964 A1 | 3/2007 | Tanaami et al. | |
| 2007/0129705 A1 | 6/2007 | Trombley et al. | |
| 2007/0161970 A1 | 7/2007 | Spohn et al. | |
| 2007/0219496 A1 | 9/2007 | Kamen et al. | |
| 2007/0276327 A1 | 11/2007 | Kalafut et al. | |
| 2008/0015406 A1 | 1/2008 | Dlugos et al. | |
| 2008/0045925 A1 | 2/2008 | Stepovich et al. | |
| 2008/0086087 A1 | 4/2008 | Spohn et al. | |
| 2008/0147147 A1 | 6/2008 | Griffiths et al. | |
| 2008/0167621 A1 | 7/2008 | Wagner et al. | |
| 2008/0183131 A1 | 7/2008 | Duchon et al. | |
| 2009/0112164 A1 | 4/2009 | Reilly et al. | |
| 2009/0216192 A1 | 8/2009 | Schriver et al. | |
| 2009/0234226 A1 | 9/2009 | Nemoto | |
| 2009/0247865 A1 | 10/2009 | Spohn et al. | |
| 2009/0247961 A1 | 10/2009 | Carlyon | |
| 2009/0312744 A1 | 12/2009 | Keeley et al. | |
| 2010/0113887 A1* | 5/2010 | Kalafut | A61B 8/481 |
| | | | 600/300 |
| 2010/0114040 A1 | 5/2010 | Schriver et al. | |
| 2010/0114064 A1 | 5/2010 | Kalafut et al. | |
| 2010/0130809 A1 | 5/2010 | Morello | |
| 2010/0222768 A1 | 9/2010 | Spohn et al. | |
| 2010/0249586 A1 | 9/2010 | Cocker et al. | |
| 2010/0262078 A1 | 10/2010 | Blomquist | |
| 2010/0331779 A1 | 12/2010 | Nystrom et al. | |
| 2011/0275988 A1 | 11/2011 | Davis et al. | |
| 2012/0089114 A1 | 4/2012 | Hemond et al. | |
| 2012/0101472 A1 | 4/2012 | Schroeder et al. | |
| 2012/0123229 A1 | 5/2012 | Butterfield et al. | |
| 2012/0178629 A1 | 7/2012 | Hudson et al. | |
| 2012/0203177 A1 | 8/2012 | Lanier, Jr. et al. | |
| 2012/0204997 A1 | 8/2012 | Winn et al. | |
| 2012/0217231 A1 | 8/2012 | Moore et al. | |
| 2012/0245560 A1 | 9/2012 | Hochman | |
| 2013/0030290 A1 | 1/2013 | Nemoto | |
| 2013/0123619 A1 | 5/2013 | Griggs | |
| 2013/0245439 A1 | 9/2013 | Small et al. | |
| 2013/0245604 A1 | 9/2013 | Kouyoumjian et al. | |
| 2013/0261993 A1 | 10/2013 | Ruchti et al. | |
| 2013/0274599 A1 | 10/2013 | Bouton et al. | |
| 2014/0027009 A1 | 1/2014 | Riley et al. | |
| 2014/0114236 A1 | 4/2014 | Gordon | |
| 2014/0142537 A1 | 5/2014 | Gibson et al. | |
| 2014/0261713 A1 | 9/2014 | Schriver et al. | |
| 2014/0276550 A1 | 9/2014 | Uram et al. | |
| 2016/0030662 A1 | 2/2016 | Uber, III et al. | |
| 2016/0224750 A1 | 8/2016 | Kethman et al. | |
| 2016/0278725 A1 | 9/2016 | Van Nijnatten | |
| 2016/0331896 A1 | 11/2016 | Nemoto et al. | |
| 2016/0346485 A1 | 12/2016 | Mohr et al. | |
| 2017/0035974 A1 | 2/2017 | Berry et al. | |
| 2017/0056603 A1 | 3/2017 | Cowan et al. | |
| 2017/0100534 A1 | 4/2017 | Fukikoshi et al. | |
| 2017/0112995 A1 | 4/2017 | Sams et al. | |
| 2017/0136424 A1 | 5/2017 | Schriver et al. | |
| 2017/0143898 A1 | 5/2017 | Grosse-Wentrup et al. | |
| 2017/0189614 A1 | 7/2017 | Mazlish et al. | |
| 2017/0196702 A1 | 7/2017 | Agarwal et al. | |
| 2017/0232173 A1 | 8/2017 | Perry et al. | |
| 2017/0258982 A1 | 9/2017 | Kemper | |
| 2017/0290971 A1 | 10/2017 | Hedmann et al. | |
| 2017/0312430 A1 | 11/2017 | Schleicher et al. | |
| 2017/0343446 A1 | 11/2017 | Ciolkosz et al. | |
| 2017/0361017 A1 | 12/2017 | Verma et al. | |
| 2018/0015274 A1 | 1/2018 | Haury et al. | |
| 2018/0133392 A1 | 5/2018 | Dembo et al. | |
| 2018/0161496 A1 | 6/2018 | Berry et al. | |
| 2018/0261496 A1 | 9/2018 | Liu et al. | |
| 2018/0280630 A1 | 10/2018 | Jiang et al. | |
| 2018/0296755 A1 | 10/2018 | Dahlin et al. | |
| 2018/0296792 A1 | 10/2018 | Hochman et al. | |
| 2019/0083699 A1 | 3/2019 | Spohn et al. | |
| 2019/0134297 A1 | 5/2019 | Kamen et al. | |
| 2020/0114074 A1 | 4/2020 | Barone et al. | |
| 2020/0129702 A1 | 4/2020 | Pedersen | |
| 2020/0146647 A1 | 5/2020 | Uber, III et al. | |
| 2020/0149948 A1 | 5/2020 | McDermott et al. | |
| 2020/0179595 A1 | 6/2020 | McDermott et al. | |
| 2020/0246541 A1 | 8/2020 | Neftel et al. | |
| 2021/0338922 A1 | 11/2021 | Uber, III et al. | |
| 2022/0001092 A1 | 1/2022 | Benamou et al. | |

FOREIGN PATENT DOCUMENTS

| | | | |
|---|---|---|---|
| CA | 2234050 | A1 | 4/1997 |
| CN | 1671428 | A | 9/2005 |
| CN | 103347552 | A | 10/2013 |
| DE | 3203594 | A1 | 8/1983 |
| DE | 3726452 | A1 | 2/1989 |
| DE | 4426387 | A1 | 8/1995 |
| DE | 19702896 | A1 | 7/1997 |
| DE | 19647701 | A1 | 5/1998 |
| DE | 19919572 | A1 | 11/2000 |
| EP | 0121216 | A1 | 10/1984 |
| EP | 0129910 | A1 | 1/1985 |
| EP | 0189491 | A1 | 8/1986 |
| EP | 0192786 | A2 | 9/1986 |
| EP | 0245160 | A1 | 11/1987 |
| EP | 0319275 | A1 | 6/1989 |
| EP | 0337924 | A2 | 10/1989 |
| EP | 0343501 | A2 | 11/1989 |
| EP | 0364966 | A1 | 4/1990 |
| EP | 0365301 | A1 | 4/1990 |
| EP | 0372152 | A1 | 6/1990 |
| EP | 0378896 | A2 | 7/1990 |
| EP | 0429191 | A2 | 5/1991 |
| EP | 0471455 | A2 | 2/1992 |
| EP | 0475563 | A1 | 3/1992 |
| EP | 0595474 | A2 | 5/1994 |
| EP | 0600448 | A2 | 6/1994 |
| EP | 0619122 | A1 | 10/1994 |

(56)                References Cited

FOREIGN PATENT DOCUMENTS

| | | | |
|---|---|---|---|
| EP | 0439711 | B1 | 5/1995 |
| EP | 0869738 | A1 | 10/1998 |
| EP | 1016427 | A2 | 7/2000 |
| EP | 1800704 | A1 | 6/2007 |
| EP | 2692375 | A1 | 2/2014 |
| EP | 2990073 | A1 | 3/2016 |
| EP | 1838365 | B1 | 2/2019 |
| FR | 2493708 | A1 | 5/1982 |
| FR | 2561949 | A1 | 10/1985 |
| GB | 201800 | A | 8/1923 |
| GB | 2252656 | A | 8/1992 |
| GB | 2328745 | A | 3/1999 |
| JP | S5017781 | A | 2/1975 |
| JP | S5815842 | A | 1/1983 |
| JP | S59214432 | A | 12/1984 |
| JP | S60194934 | A | 10/1985 |
| JP | S60194935 | A | 10/1985 |
| JP | S60253197 | A | 12/1985 |
| JP | S62216199 | A | 9/1987 |
| JP | S6340538 | A | 2/1988 |
| JP | S63290547 | A | 11/1988 |
| JP | H01207038 | A | 8/1989 |
| JP | H02224647 | A | 9/1990 |
| JP | H02234747 | A | 9/1990 |
| JP | H0355040 | A | 3/1991 |
| JP | H04115677 | A | 4/1992 |
| JP | H0584296 | A | 4/1993 |
| JP | H07178169 | A | 7/1995 |
| JP | H0849598 | A | 2/1996 |
| JP | H0999034 | A | 4/1997 |
| JP | H10211198 | A | 8/1998 |
| JP | 2000175900 | A | 6/2000 |
| JP | 2003102724 | A | 4/2003 |
| JP | 2003116843 | A | 4/2003 |
| JP | 2003210456 | A | 7/2003 |
| JP | 2003225234 | A | 8/2003 |
| JP | 2004174008 | A | 6/2004 |
| JP | 2004236849 | A | 8/2004 |
| JP | 2004298550 | A | 10/2004 |
| JP | 2011234774 | A | 11/2011 |
| JP | 4960180 | B2 | 6/2012 |
| JP | 5063593 | B2 | 10/2012 |
| JP | 5203971 | B2 | 6/2013 |
| JP | 5227791 | B2 | 7/2013 |
| JP | 5485885 | B2 | 5/2014 |
| JP | 5490840 | B2 | 5/2014 |
| JP | 5511409 | B2 | 6/2014 |
| JP | 5882595 | B2 | 3/2016 |
| JP | 5897798 | B2 | 3/2016 |
| JP | 6552258 | B2 | 7/2019 |
| JP | 6618673 | B2 | 12/2019 |
| JP | 6644469 | B2 | 2/2020 |
| JP | 6676377 | B2 | 4/2020 |
| JP | 6792104 | B2 | 11/2020 |
| JP | 6839853 | B2 | 3/2021 |
| WO | 8001754 | A1 | 9/1980 |
| WO | 8500292 | A1 | 1/1985 |
| WO | 8803815 | A1 | 6/1988 |
| WO | 9114232 | A1 | 9/1991 |
| WO | 9114233 | A1 | 9/1991 |
| WO | 9315658 | A1 | 8/1993 |
| WO | 9325141 | A1 | 12/1993 |
| WO | 9415664 | A1 | 7/1994 |
| WO | 9632975 | A1 | 10/1996 |
| WO | 9712550 | A1 | 4/1997 |
| WO | 9820919 | A1 | 5/1998 |
| WO | 9924095 | A2 | 5/1999 |
| WO | 0061216 | A1 | 10/2000 |
| WO | 0141835 | A2 | 6/2001 |
| WO | WO-0180928 | A2 * | 11/2001 | ........... A61M 39/26 |
| WO | 03015633 | A1 | 2/2003 |
| WO | 2004012787 | A2 | 2/2004 |
| WO | 2004035116 | A1 | 4/2004 |
| WO | 2004091688 | A2 | 10/2004 |
| WO | 2005016165 | A1 | 2/2005 |
| WO | 2005035995 | A1 | 4/2005 |
| WO | 2006042093 | A1 | 4/2006 |
| WO | 2006074415 | A2 | 7/2006 |
| WO | 2007079016 | A2 | 7/2007 |
| WO | 2007092618 | A2 | 8/2007 |
| WO | 2007116840 | A1 | 10/2007 |
| WO | 2007116862 | A1 | 10/2007 |
| WO | 2007116891 | A1 | 10/2007 |
| WO | 2007133942 | A2 | 11/2007 |
| WO | 2008078604 | A1 | 7/2008 |
| WO | 2008106108 | A1 | 9/2008 |
| WO | 2008153831 | A2 | 12/2008 |
| WO | 2009026420 | A1 | 2/2009 |
| WO | 2009042577 | A2 | 4/2009 |
| WO | 2009051995 | A1 | 4/2009 |
| WO | 2010027636 | A1 | 3/2010 |
| WO | 2010117841 | A1 | 10/2010 |
| WO | 2011002744 | A1 | 1/2011 |
| WO | 2011011346 | A1 | 1/2011 |
| WO | 2011097487 | A2 | 8/2011 |
| WO | 2011125303 | A1 | 10/2011 |
| WO | 2012048277 | A2 | 4/2012 |
| WO | 2012155035 | A1 | 11/2012 |
| WO | 2013043868 | A1 | 3/2013 |
| WO | 2014035672 | A2 | 3/2014 |
| WO | 2014049656 | A1 | 4/2014 |
| WO | 2014144651 | A2 | 9/2014 |
| WO | 2014179326 | A1 | 11/2014 |
| WO | 2014190264 | A1 | 11/2014 |
| WO | 2015106107 | A1 | 7/2015 |
| WO | 2015164783 | A1 | 10/2015 |
| WO | 2016004329 | A1 | 1/2016 |
| WO | 2016112163 | A1 | 7/2016 |
| WO | 2016172467 | A1 | 10/2016 |
| WO | 2016191485 | A1 | 12/2016 |
| WO | 2017012781 | A1 | 1/2017 |
| WO | 2017038575 | A1 | 3/2017 |
| WO | 2017096072 | A1 | 6/2017 |
| WO | 2017152036 | A1 | 9/2017 |
| WO | 2018060505 | A1 | 4/2018 |
| WO | 2018075379 | A1 | 4/2018 |
| WO | 2018075386 | A1 | 4/2018 |
| WO | 2018089882 | A1 | 5/2018 |
| WO | 2018144369 | A1 | 8/2018 |
| WO | 2019046299 | A1 | 3/2019 |

OTHER PUBLICATIONS

Awai, K., et al., "Effect of contrast material injection duration and rate on aortic peak time and peak enhancement at dynamic CT involving injection protocol with dose tailored to patient weight," Radiology, vol. 230, Issue 1, pp. 142-150, 2004.

Bae, et al. "Aortic and Hepatic Contrast Medium Enhancement at CT—Part I, Prediction with a Computer Model", Radiology 1998;207:647-655.

Bae, K.T., et al., "Multiphasic Injection Method for Uniform Prolonged Vascular Enhancement at CT Angiography: Pharmacokinetic Analysis and Experimental Porcine Model," Radiology, vol. 216, Issue 3, pp. 872-880 (Sep. 2000).

Bae, K.T. et al., "Peak Contrast Enhancement in CT and MR Angiography: When Does it Occur and Why? Pharmacokinetic Study in a Porcine Model", Radiology, vol. 227, Jun. 2003, pp. 809-816.

Bae, K.T., et al., "Uniform vascular contrast enhancement and reduced contrast medium volume achieved by using exponentially decelerated contrast material injection method," Radiology, vol. 231, Issue 3, pp. 732-736, 2004.

Baker, Aaron; et al. "Fluid Mechanics Analysis of a Spring-Loaded Jet Injector." IEEE Transactions on Biomedical Engineering, vol. 46, No. 2, Feb. 1999.

Becker, C.R., et al., "Optimal contrast application for cardiac 4-detector-row computed tomography," Investigative Radiology, vol. 38, Issue 11, pp. 690-694 (Nov. 2003).

Blomley, M.J.K. and Dawson, P., "Bolus Dynamics: Theoretical and Experimental Aspects," The Brit. J. ofRadiology, vol. 70, No. 832, pp. 351-359 (Apr. 1997).

(56) References Cited

OTHER PUBLICATIONS

Brunette J.; et al., "Comparative rheology of low- and iso-osmolarity contrast agents at different temperature", Catheterization and Cardiovascular Interventions, 2008, vol. 71 Issue No. 1, 78-83.

Cademartiri, F. and Luccichenti, G., et al. "Sixteen-row multislice computed tomography: basic concepts, protocols, and enhanced clinical applications," Seminars in Ultrasound, CT and MRI, vol. 25, Issue 1, pp. 2-16, 2004.

Dardik, H. et al., "Remote Hydraulic Syringe Actuator," Arch. Surg., vol. 115, Issue 1, Jan. 1980.

Dawson, P. and Blomley, M., "The value of mathematical modelling in understanding contrast enhancement in CT with particular reference to the detection of hypovascular liver metastases," European Journal of Radiology, vol. 41, Issue 3, pp. 222-236 (Mar. 2002).

"Digital Injector for Angiography", Sias. (Sep. 7, 1993).

Disposable Low-Cost Catheter Tip Sensor Measures Blood Pressure during Surgery, Sensor (Jul. 1989).

EZ Chem Brochure, E-Z-EM, Inc. (Jul. 2007).

Fisher, M.E. and Teo, K.L., "Optimal insulin infusion resulting from a mathematical model of blood glucose dynamics", IEEE Transactions on Biomedical Engineering, vol. 36, Issue 4, pp. 479-486, 1989.

Flegal, K.M., et al., "Prevalence and trends in obesity among US adults," JAMA, 2002, vol. 288, Issue 14, pp. 1-4, (1999-2000).

Fleischmann, D. and Hittmair, K., "Mathematical analysis of arterial enhancement and optimization of bolus geometry for CT angiography using the discrete Fourier transform," Journal of Computer Assisted Tomography, vol. 23, Issue 3, pp. 474-484 (May/Jun. 1999).

Fleischmann, D., "Contrast Medium Injection Technique," In: U. Joseph Schoepf: "Multidetector—Row CT of The Thorax," pp. 47-59 (Jan. 22, 2004).

Fleischmann, D., "Present and Future Trends in Multiple Detector-Row CT Applications; CT Angiography", European Radiology, vol. 12, Issue 2, Supplement 2, Jul. 2002, pp. s11-s15.

Gardiner, G. A., et al., "Selective Coronary Angiography Using a Power Injector," AJR Am J Roentgenol., vol. 146, Issue 4, pp. 831-833 (Apr. 1986).

Garrett, J. S., et al., "Measurement of cardiac output by cine computed tomography," The American Journal of Cardiology, vol. 56, Issue 10, pp. 657-661, 1985.

Gembicki, F.W., "Vector Optimization for Control with Performance and Parameter Sensitivity Indices," PhD Thesis Case Western Reserve University, 1974.

Gentilini A., et al., "A new paradigm for the closed-loop intraoperative administration of analgesics in humans," IEEE Transactions on Biomedical Engineering, vol. 49, Issue 4, pp. 289-299 (Apr. 2002).

Gerlowski L.E. and Jain R.K., "Physiologically Based Pharmacokinetic Modeling: Principles and Applications," Journal of Pharmaceutical Sciences, vol. 72, pp. 1104-1125, Oct. 1983.

Goss, J. E., et al., "Power injection of contrast media during percutaneous transluminal coronary artery angioplasty," Catheterization and Cardiovascular Diagnosis, vol. 16, Issue 3, pp. 195-198 (Mar. 1989).

Grant, S.C.D. et al., "Reduction of Radiation Exposure to the Cardiologist during Coronary Angiography by the Use of a Remotely Controlled Mechanical Pump for Injection of Contrast Medium," Catheterization and Cardiovascular Diagnosis, vol. 25, Issue 2, pp. 107-109 (Feb. 1992).

Hackstein, N. et al., "Glomerular Filtration Rate Measured by Using Triphasic Helical CT with a Two-Point Patlak Plot Technique," Radiology, vol. 230, Issue 1, pp. 221-226, Jan. 2004.

Hansen, P.C, Regularization tools: a MATLAB package for analysis and solution of discrete ill-posed problems, Numerical Algorithms, vol. 6, Issue 1, pp. 35, 1994.

Hansen, P.C., "The truncated SVD as a method for regularization," BIT Numerical Mathematics, vol. 27, Issue 4, pp. 534-555, 1987.

Harris P., H. D. "The Human Pulmonary Circulation," Edinburgh, Churchill Livingstone, (Appendix I), 1986.

Hayes, M., "Statistical Digital Signal Processing and Modeling", New York, New York, Wiley and Sons, 1996, pp. 154-177, (Prony's method).

Heiken; J.P. et al., "Dynamic Contrast-Enhanced CT of the Liver: Comparison of Contrast Medium Injection Rates and Uniphasic and Biphasic Injection Protocols", Radiology, May 1993, vol. 187, No. 2, pp. 327-331.

"Infus O.R. Multi-Drug Syringe Pump with Smart Labels," Bard MedSystems Division Inc., pp. 2693-2696 (2005).

"International Preliminary Report on Patentability from PCT Application No. PCT/US2018/048282", Mar. 12, 2020.

Ireland, M.A., et al., "Safety and Convenience of a Mechanical Injector Pump for Coronary Angiography," Catheterization and Cardiovascular Diagnosis, vol. 16, Issue 3, pp. 199-201 (1989).

Jacobs, J.R., "Algorithm for optimal linear model-based control with application to pharmacokinetic model-driven drug delivery," IEEE Transactions on Biomedical Engineering, vol. 37, Issue 1, pp. 107-109 (Jan. 1990).

Korosec, F.R., "Physical Principles of Phase-Contrast, Time-of-Flight, and Contrast-Enhanced MR Angiography," 41st Annual Meeting of American Association of Physicists in Medicine, Jul. 25-29, 1999.

Korosec, Frank, "Basic Principles of Phase-contrast, Time-of-flight, and Contrast-enhanced MR Angiography", 1999.

Krause, W, "Application of pharmacokinetics to computed tomography: injection rates and schemes: mono-, bi-, or multiphasic?," Investigative Radiology, vol. 31, Issue 2, pp. 91-100, Feb. 1996.

Krieger, R. A., "CO2-Power-Assisted Hand-Held Syringe: Better Visualization during Diagnostic and InterventionalAngiography," Cathet Cardiovasc Diagn., vol. 19, Issue 2, pp. 123-128 (Feb. 1990).

Liebel-Flarsheim Company, "Angiomat 6000 Digital Injection System-Operator's Manual", Document No. 600950, Rev. 1, Jan. 1990.

Mahnken, A. H., et al., "Determination of cardiac output with multislice spiral computed tomography: a validation study," Investigative Radiology, vol. 39, Issue 8, pp. 451-454, Aug. 2004.

Mahnken, A. H., et al., "Measurement of cardiac output from a test-bolus injection in multislice computed tomography," European Radiology, vol. 13, Issue 11, pp. 2498-2504, 2003.

Mark V/Mark V Plus Injector Operation Manual KMP 805P Rev. B. Medrad, Inc, 1990.

Mcclellan, J.H., "Parametric Signal Modeling," Chapter 1 in Advanced Topics in Signal Processing, Pentice-Hall, Englewood Cliffs, NJ (1988).

MCT and MCT Plus Injection Systems Operation Manual KMP 810P, Medrad, Inc, 1991.

Morden Peter.; et al., "The Role of Saline Flush Injection Rate in Displacement of CT Injectable Peripherally Inserted Central Catheter Tip During Power Injection of Contrast Material", AJR, Jan. 2014, 202, W13-W18.

Neatpisarnvanit, C. and Boston, J.R., "Estimation of plasma insulin from plasma glucose", IEEE Transactions on Biomedical Engineering, vol. 49, Issue 11, pp. 1253-1259, 2002.

Angiography, Catheterization and Cardiovascular Diagnosis, vol. 19, pp. 123-128, 1990.

Awai Kazuo; et al., "Aortic and Hepatic Enhancement and Tumor-to-Liver Contrast: Analysis of the Effect of Different Concentrations of Contrast Material at Multi-Detector Row Helical CT.", Radiology, 2002, vol. 224; Issue 3., 757-763.

Swiss; Medical Care., "CT Expres Contrast Media Delivery System Operation Manual Rev 1", 2004.

Ostergaard, L., et al., "High resolution measurement of cerebral blood flow using intravascular tracer poluspassages. Part 1: Mathematical approach and statistical analysis," Magnetic Resonance in Medicine, vol. 36, Issue 5,pp. 715-725 (Nov. 1996).

Ostergaard, L., et al., "High resolution measurement of cerebral blood flow using intravascular tracer boluspassages. Part II: Experimental comparison and preliminary results," Magn Reson Med, vol. 36, Issue 5, pp. 726-736(Nov. 1996).

Parker, K.J., et al., "A Particulate Contrast Agent With Potential For Ultrasound Imaging of Liver," Ultrasound in Medicine & Biology, vol. 13, Issue 9, pp. 555-566 (Sep. 1987).

(56)                    References Cited

OTHER PUBLICATIONS

Rosen, B.R. et al., "Perfusion Imaging with NMR Contrast Agents," Magentic Resonance in Medicine, vol. 14, No. 2, pp. 249-265, May 1, 1990.

Sablayrolles, J-L, "Cardiac CT: Experience from Daily Practice", Advance Ct, A GE Healthcare Publication. Aug. 2004.

Stevens, M.A., et al. "A Prospective Randomized Trial of Prevention Measures in Patients at High Risk for Contrast Nephropathy," J. of the ACC, vol. 33, Issue 2, pp. 403-411, Feb. 1999.

Wada D.R. and Ward; D.S., "The hybrid model: a new pharmacokinetic model for computer-controlled infusion pumps", IEEE Transactions on Biomedical Engineering, 1994, vol. 41, Issue 2, pp. 134-142.

Wada, D.R. and Ward, D.S., "Open loop control of multiple drug effects in anesthesia", IEEE Transactions on Biomedical Engineering, vol. 42, Issue 7, pp. 666-677, 1995.

Yamashita, Y. et al., "Abdominal Helical CT: Evaluation of Optimal Doses of Intravenous Contrast Material—A Prospective Randomized Study," Radiology, vol. 216, Issue 3, pp. 718-723, Sep. 1, 2000.

"The Solution for Our IV Formulas", IV 6500 Formulator Volumetric Pump, Valley Lab Inc., 39C 9410976 0000071 s, E-39-15, pp. 3399-3400, As early as 1980.

Brenner et al., Radiation Exposure From Medical Imaging: Time to Regulate?, JAMA, Jul. 14, 2010, vol. 304 No 2, 208-209.

Extravasation Sensor Support System LD Operation Manual, Nemoto Kyorindo Co Ltd, Sep. 13, 2012, Rev 4.

Kern et al, Multi-Sensor Activity Context Detection for Wearable Computing, 2016.

McCullough, et al., "Risk Prediction of Contrast-Induced Nephropathy", The American Journal of Cardiology, Sep. 18, 2006, vol. 98.

Sachiko T. Cochran et al., Trends in Adverse Events After IV Administration of Contrast Media, Am. J. of Roentgenology, Jun. 2001, 176, 1385-1388.

Shaqdan et al., Incidence of contrast medium extravastion for CT and MRI in a large academic medical centre: A report on 502,391 injections, Clinical Radiology, Elsevier, 2014, 69, 1264-1272.

Vinod et al., Acute compartment syndrome of hand resulting from radiograph contrast iohexol exravasation, Journal of Pharmacology and Pharmacotherapeutics, 2016, 44-7, 7-44.

* cited by examiner

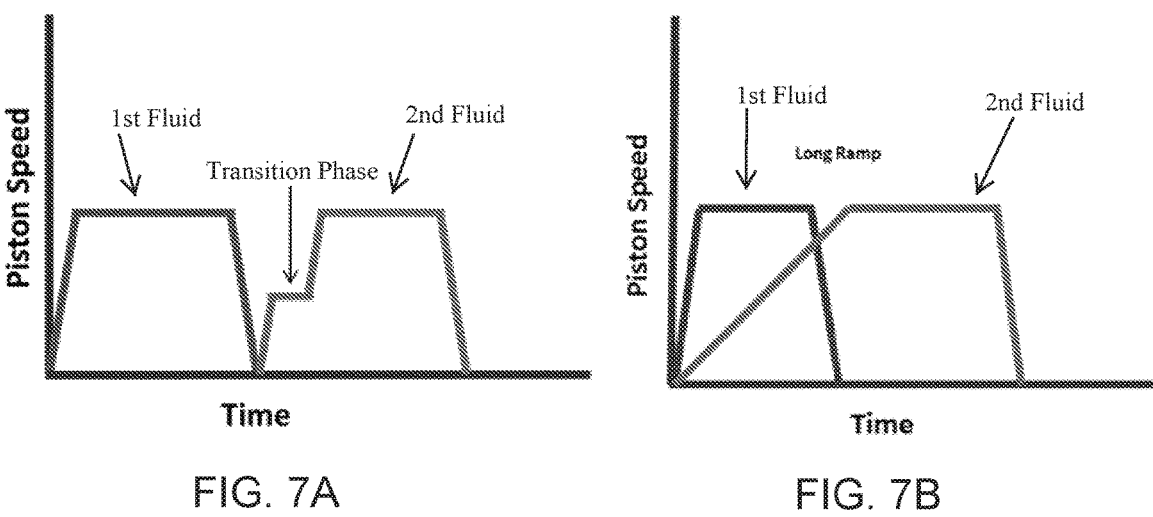
FIG. 7A
FIG. 7B
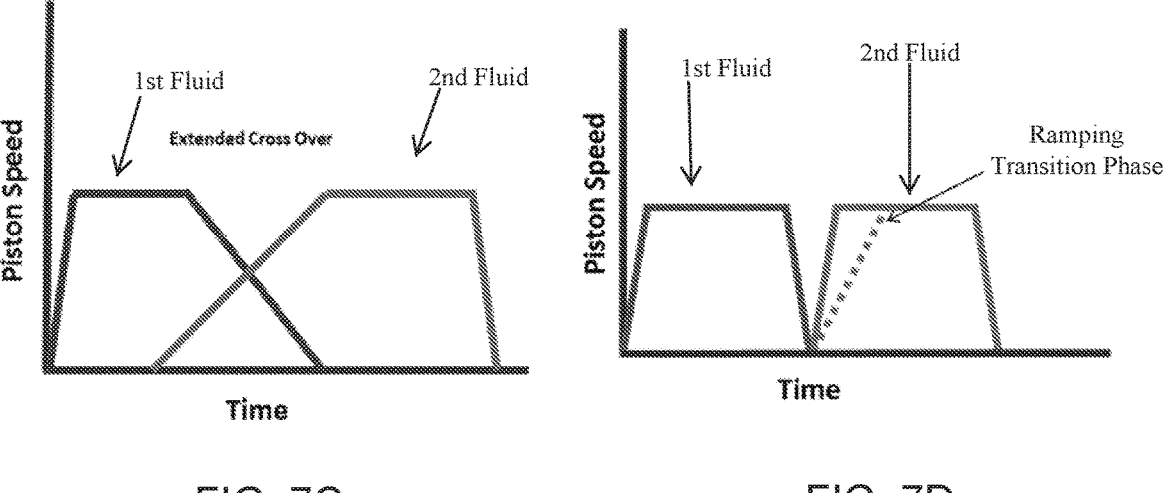
FIG. 7C
FIG. 7D

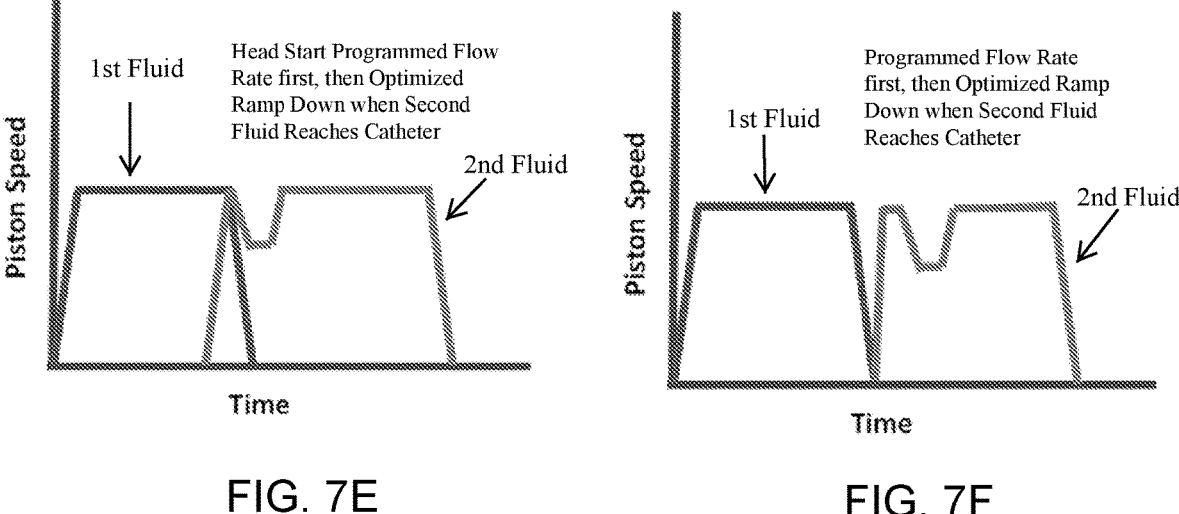
FIG. 7E
FIG. 7F
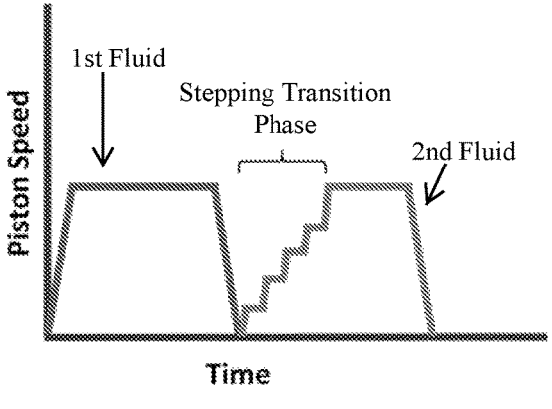
FIG. 7G
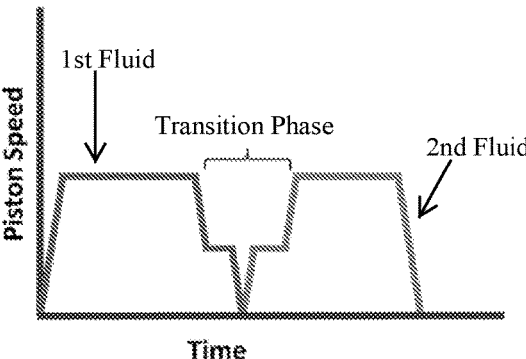
FIG. 7H

Time (s)

| First Phase Flow Rate (mL/s) | First Phase Pressure (kPa) | Scaling Factor (Catheter Gauge) | Second Phase Flow Rate (mL/s) | Second Phase Predicted Pressure (kPa) |
|---|---|---|---|---|
| 1 | 0 | 18 | 1 | 62 |
| 1 | 207 | 18 | 1 | 62 |
| 1 | 483 | 18 | 1 | 62 |
| 1 | 758 | 24 | 1 | 103 |
| 1 | 1034 | 24 | 1 | 103 |
| 1 | 1310 | 24 | 1 | 103 |
| 1 | 1586 | 24 | 1 | 103 |
| 1 | 1862 | 24 | 1 | 103 |
| 2 | 0 | 18 | 2 | 103 |
| 2 | 276 | 18 | 2 | 103 |
| 2 | 552 | 18 | 2 | 103 |
| 2 | 827 | 24 | 2 | 241 |
| 2 | 1103 | 24 | 2 | 241 |
| 2 | 1379 | 24 | 2 | 241 |
| 2 | 1655 | 24 | 2 | 241 |
| 2 | 1931 | 24 | 2 | 241 |
| 3 | 69 | 18 | 3 | 145 |
| 3 | 345 | 18 | 3 | 145 |
| 3 | 621 | 18 | 3 | 145 |
| 3 | 896 | 18 | 3 | 145 |
| 3 | 1172 | 24 | 3 | 448 |
| 3 | 1448 | 24 | 3 | 448 |
| 3 | 1724 | 24 | 3 | 448 |
| 3 | 1999 | 24 | 3 | 448 |
| 4 | 138 | 18 | 4 | 186 |
| 4 | 414 | 18 | 4 | 186 |
| 4 | 689 | 18 | 4 | 186 |
| 4 | 965 | 18 | 4 | 186 |
| 4 | 1241 | 18 | 4 | 186 |
| 4 | 1517 | 24 | 4 | 724 |
| 4 | 1793 | 24 | 4 | 724 |
| 4 | 2068 | 24 | 4 | 724 |
| 5 | 207 | 18 | 5 | 241 |
| 5 | 483 | 18 | 5 | 241 |
| 5 | 758 | 18 | 5 | 241 |
| 5 | 1034 | 18 | 5 | 241 |
| 5 | 1310 | 18 | 5 | 241 |
| 5 | 1586 | 18 | 5 | 241 |
| 5 | 1862 | 24 | 5 | 1351 |

FIG. 10

Saline Pressure vs. Flow Rate (18 Gauge)

$$y = 4.3862x^2 + 15.192x + 48.871$$
$$R^2 = 0.9991$$

System Compliance Characterization
Rank 7 Eqn 302461977 $z^{-1} = a + b/x^{0.5} + cy^{0.5}$
$r^2 = 0.98825093$ DF Adj $r^2 = 0.98800951$ FitStdErr = 0.19467277 Fstat = 6182.3152
a = 0.11422056 b=10.39086
c = -0.014863432

General Workflow

SYSTEM AND METHOD HAVING TRANSITION PHASE IN MULTI-PHASE INJECTION PROTOCOL

CROSS REFERENCE TO RELATED APPLICATIONS

This application is a § U.S. national phase application under 35 U.S.C. § 371 of PCT International Application No. PCT/US2018/048282, filed 28 Aug. 2018 and claims priority to U.S. Provisional Application No. 62/552,494, titled "System and Method Having Transition phase in Multi-Phase Injection Protocol" and filed on 31 Aug. 2017, the disclosures of which are incorporated herein in their entirety.

BACKGROUND OF THE DISCLOSURE

Field of the Disclosure

The present disclosure relates generally to a system and method for controlling a fluid injector. More particularly, the present disclosure relates to a system and method for controlling the fluid injector utilizing a multi-phase injection protocol having a transition phase.

Description of Related Art

In many medical diagnostic and therapeutic procedures, a medical practitioner, such as a physician, injects a patient with one or more medical fluids. In recent years, a number of fluid delivery systems having injector-actuated syringes and fluid injectors for pressurized injection of fluids, such as a contrast solution (often referred to simply as "contrast"), a flushing agent, such as saline or Ringer's lactate, and other medical fluids have been developed for use in procedures such as angiography (CV), computed tomography (CT), ultrasound, magnetic resonance imaging (MRI), positron emission tomography (PET), and other imaging procedures. In general, these fluid delivery systems are designed to deliver a preset amount of fluid at a desired flow rate.

An actual flow rate (or delivered volume) of fluid that is delivered to the patient is targeted to be as close as possible to the desired flow rate (or desired volume). However, the actual performance of the fluid delivery system is a function of many factors due to overall impedance and capacitance of the fluid delivery system. In certain delivery procedures, impedance and capacitance of the fluid delivery system may cause a fluid flow over-rate, under-rate (or volume over- or under-delivery) from a desired flow rate (or desired volume), and fluctuations in fluid flow, particularly when transitioning from one fluid type to another fluid type.

While various approaches exist for characterizing the performance of a fluid delivery system and correlating the desired performance with actual performance in terms of fluid flow rate and volume delivered, these approaches do not address the differences between desired and actual performance due to impedance and/or capacitance of the fluid delivery system in a comprehensive manner. As a result, existing approaches fail to address the under-delivery or over-delivery of fluid resulting from system impedance and/or capacitance. As a result, less than optimal injection boluses or volumes may result and/or operation of the fluid delivery system can result in relatively large amounts of wasted fluid.

SUMMARY OF DISCLOSURE

In one example of the present disclosure, a method of delivering a multi-phase fluid injection to a patient via a fluid injector comprising two or more fluid reservoirs is described. The method may comprise injecting a first fluid of the fluid injection from at least a first fluid reservoir, the first fluid having a first viscosity, wherein the first fluid is delivered to the patient at a first predetermined flow rate; injecting an initial portion of at least a second fluid of the fluid injection from at least a second fluid reservoir, the second fluid having a second viscosity different from the first viscosity, wherein the initial portion of the second fluid is delivered to the patient with a flow rate profile different from a second predetermined flow rate for a specified intermediate time interval; and injecting a remaining portion of the second fluid of the fluid injection at a flow rate at least equal to the second predetermined flow rate.

In specific embodiments the first viscosity is greater than the second viscosity. The first and second fluid may be a contrast medium, saline, Ringer's lactate, or other medical fluid. In particular embodiments, the first fluid may be selected from the group consisting of a contrast media, and a mixture of a specific ratio of the contrast media and saline or other flushing fluid such as water or Ringer's lactate, and wherein the second fluid may be selected from the group consisting of saline or other flushing fluid such as water or Ringer's lactate and a mixture of a second specific ratio of the contrast media and saline or other flushing fluid such as water or Ringer's lactate. According to certain aspects, the second predetermined flow rate may be substantially the same as the first predetermined flow rate.

According to various embodiments, the flow rate profile of the initial portion of the at least second fluid may be different than the first predetermined flow rate and/or the second predetermined flow rate. In certain embodiments, the flow rate profile of at least the initial portion of the at least second fluid is delivered at a flow rate lower than the first predetermined flow rate. In other embodiments, the flow rate profile of at least the initial portion of the at least second fluid is delivered at a flow rate that varies between zero and the first predetermined flow rate or the second predetermined flow rate over the specified intermediate time interval. For example, the flow rate profile of the at least the initial portion may start at a lower flow rate and increase over the specified intermediate time interval, such increasing to the second predetermined flow rate by the end of the initial portion of the at least second fluid.

According to various embodiments of the methods described herein, injecting the initial portion of at least the second fluid may comprise injecting the initial portion of at least the second fluid at an intermediate flow rate lower than the second predetermined flow rate over the specified intermediate time interval, wherein the specified intermediate time interval is selected to allow a residual portion of the first fluid to pass through a fluid line to the patient before beginning the step of injecting the remaining portion of the second fluid, wherein the specified intermediate time interval is based on system architecture; a capacitance of at least one of the first fluid reservoir and the second fluid reservoir, a length of the fluid line, a diameter of the fluid line, a volume of the fluid line, the length of a catheter, the diameter of the catheter, the volume of the catheter and any combination thereof. In various embodiments of the methods, a volume of the initial portion of the second fluid of the fluid injection may be determined by one or more of a volume capacity of a fluid line, optionally including the catheter volume capacity, between the second fluid reservoir and the patient, a capacitance of at least one of the first fluid reservoir and the second fluid reservoir, and an injection system compliance.

In specific embodiments, the methods may further comprise inputting by a system user the flow rate profile of the second fluid including the transition phase based at least in part on one or more parameters selected from the group consisting of a table of injection protocols, first phase flow rate, second phase flow rate, transition flow rate, catheter volume, catheter diameter, catheter length, volume of the fluid line between the fluid reservoir and the patient, diameter of the fluid line, length of the fluid line, viscosity of the first fluid, viscosity of the second fluid, temperature of the first fluid, temperature of the second fluid, programmed volume of the first fluid to be delivered, and programmed volume of the second fluid to be delivered. The tables may be prepared by a system manufacturer and programmed into a processor associated with the fluid injector system, may be developed independently by the system user or some other third party to be utilized with various injection protocols for the fluid injection system.

According to specific embodiments, the flow rate profile of the initial portion is selected to minimize flow rate deviations over the specified intermediate time interval. In particular embodiments, the flow rate profile of the initial portion may be calculated based on the following equation:

$$Q(\text{transition}) = Q(\text{programmed}) - Q(\text{adjusted})$$

wherein Q(transition) is a desired flow rate profile over a transition between the first fluid to at least the second fluid by adjusting the drive member movement (speed over distance) to control the fluid flow out of the catheter tip; Q(programmed) is a desired flow rate profile for the at least the second fluid; and Q(adjusted) is a necessary adjustment of the flow rate of the second fluid so that Q(transition) at the transition between the first fluid and at least the second fluid results in a fluid flow rate from the catheter that is substantially similar to Q(programmed). In other embodiments, the flow rate profile of the initial portion may be calculated based on the following equation:

$$Q(t) = Q(p) - (C(1) - C(2))/t(t),$$

wherein Q(t) is the intermediate flow rate, Q(p) is the second predetermined flow rate, C(1) is a steady state system compliance during the first fluid phase, C(2) is a system compliance during the second fluid injection, and t(t) is a derived time for delivering the volume associated with the system compliance (C(2)). According to various embodiments, the system compliance during the first fluid injection comprises a first compliance factor associated with one or more of the first fluid reservoir, a first fluid delivery mechanism, and a tubing set in operative fluid communication the first fluid reservoir, and the system compliance during the second fluid injection comprises a second compliance factor associated with one or more of the second fluid reservoir, a second fluid delivery mechanism, and a tubing set in operative communication the second fluid reservoir. The system compliance of the first reservoir and/or the at least the second reservoir may be measured, for example using a flow sensor in the fluid path between the reservoir(s) and the catheter. Alternatively the one or both of the system compliance of the first reservoir and/or the at least the second reservoir may be may be predicted based on factors of the fluid injector, the first or second fluid reservoir, and the first or second fluid, respectively.

According to various embodiments of the present disclosure, first and second fluid reservoirs may be independently selected from the group consisting of a syringe, a peristaltic pump, and a compressible bag. In specific embodiments, the first fluid reservoir is a first syringe operatively connected to a first drive member of the fluid injector and at least the second fluid reservoir is at least a second syringe operatively connected to at least a second drive member of the fluid injector.

According to other embodiments, the present disclosure describes a fluid injector system for delivering a multi-phase fluid injection to a patient. The fluid injector system may comprise at least one first syringe configured to contain a first fluid of the multi-phase fluid injection, the first fluid having a first viscosity; at least one first drive member operatively connected with the at least one first syringe, the at least one first drive member being operable to dispense the first fluid of the multi-phase fluid injection; at least one second syringe configured to contain a second fluid of the multi-phase fluid injection, the second fluid having a second viscosity different from the first viscosity; at least one second drive member operatively connected with the at least one second syringe, the at least one second piston being operable to dispense the second fluid of the multi-phase fluid injection; a fluid line connected to the at least one first syringe and the at least one second syringe, and configured to deliver at least one of the first fluid of the multi-phase fluid injection from the at least one first syringe to the patient and the second fluid of the multi-phase fluid injection from the at least one second syringe to the patient; and a control device configured to control movement of the first drive member associated with the at least one first syringe and movement of the at least one second drive member associated with the at least one second syringe to control the delivery of the first fluid and the second fluid of the multi-phase fluid injection to the patient. The control device may be configured to control the first drive member to inject the first fluid at a first predetermined flow rate, to control the at least one second drive member to inject an initial portion of at least the second fluid of the fluid injection from the at least one second syringe at an intermediate flow rate profile different from a second predetermined flow rate for a specified intermediate time, and to inject a remaining portion of the second fluid at least equal to the second predetermined flow rate, wherein the second fluid has a second viscosity different from the first viscosity.

According to various embodiments, the first viscosity is greater than the second viscosity. The first and second fluid may be a contrast medium, a saline, Ringer's lactate, other flushing fluid, or other medical fluid. In particular embodiments, the first fluid may be selected from the group consisting of a contrast media, and a mixture of a specific ratio of the contrast media and saline, and wherein the second fluid may be selected from the group consisting of saline, Ringer's lactate, and a mixture of a second specific ratio of the contrast media and saline. According to certain aspects, the second predetermined flow rate may be substantially the same as the first predetermined flow rate.

In various embodiments of the fluid injector system, the first predetermined flow rate may be substantially the same as the second predetermined flow rate. In other embodiments, the flow rate profile of at least the initial portion of the at least second fluid may be delivered at a flow rate lower than the first predetermined flow rate, or the flow rate profile of at least the initial portion of the at least second fluid may be delivered at a flow rate that varies between zero and the first predetermined flow rate or between zero and the second predetermined flow rate over the specified intermediate time interval. According to certain embodiments, the first predetermined flow rate may be greater than the second predetermined flow rate.

According to various embodiments of the fluid injector system, control device may be configured to time an injection of the initial portion of at least the second fluid comprises injecting the initial portion of at least the second fluid at an intermediate flow rate lower than the second predetermined flow rate over the specified intermediate time interval, wherein the specified intermediate time interval is selected to allow a residual portion of the first fluid to pass through a fluid line to the patient before beginning the step of injecting the remaining portion of the second fluid, wherein the specified intermediate time interval is based on one or more of system architecture; a capacitance of at least one of the first fluid reservoir and the second fluid reservoir, a length of the fluid line, a diameter of the fluid line, a volume of the fluid line, the capacitance of the fluid line and an associated catheter, and any combination thereof.

According to certain embodiments of the fluid injection system, the flow rate profile of the initial portion is calculated based on the following equation:

$$Q(\text{transition})=Q(\text{programmed})-Q(\text{adjusted})$$

wherein Q(transition) is a desired flow rate profile over a transition between the first fluid to at least the second fluid by adjusting the drive member movement (speed over distance) to control the fluid flow out of the catheter tip; Q(programmed) is a desired flow rate profile for the at least the second fluid; and Q(adjusted) is a necessary adjustment of the flow rate of the second fluid so that Q(transition) at the transition between the first fluid and at least the second fluid results in a fluid flow rate from the catheter that is substantially similar to Q(programmed). According to specific embodiments, the intermediate time may be substantially question to the time that it takes for the remaining amount of the first fluid to be delivered out of the fluid line, for example by dividing the volume of the fluid line and catheter by the programmed flow rate.

According to other embodiments of the fluid injector system, the flow rate profile of the initial portion is calculated based on the following equation:

$$Q(t)=Q(p)-(C(1)-C(2))/t(t),$$

wherein Q(t) is the intermediate flow rate, Q(p) is the second predetermined flow rate, C(1) is a steady state system compliance during the first fluid phase, C(2) is a system compliance during the second fluid injection, and t(t) is a derived time for delivering the volume associated with the system compliance (C(2)).

Various aspects of the system and method for controlling a fluid injector utilizing a multi-phase injection protocol having a transition phase are disclosed in one or more of the following numbered clauses:

Clause 1. A method of delivering a multi-phase fluid injection to a patient via a fluid injector comprising two or more fluid reservoirs, the method comprising: injecting a first fluid of the fluid injection from at least a first fluid reservoir, the first fluid having a first viscosity, wherein the first fluid is delivered to the patient at a first predetermined flow rate; injecting an initial portion of at least a second fluid of the fluid injection from at least a second fluid reservoir, the second fluid having a second viscosity different from the first viscosity, wherein the initial portion of the second fluid is delivered to the patient with a flow rate profile different from a second predetermined flow rate for a specified intermediate time interval or intermediate fluid volume; and injecting a remaining portion of the second fluid of the fluid injection at a flow rate at least equal to the second predetermined flow rate.

Clause 2. The method according to clause 1, wherein the first viscosity is greater than the second viscosity.

Clause 3. The method according to clause 1 or clause 2, wherein first fluid is selected from the group consisting of a contrast media, and a mixture of a specific ratio of the contrast media and saline, and wherein the second fluid is selected from the group consisting of saline and a mixture of a second specific ratio of the contrast media and saline.

Clause 4. The method according to any of clauses 1 to 3, wherein the second predetermined flow rate is substantially the same as the first predetermined flow rate.

Clause 5. The method according to any of clauses 1 to 4, wherein the flow rate profile of at least the initial portion of the at least second fluid is delivered at a flow rate lower than the first predetermined flow rate.

Clause 6. The method according to any of clauses 1 to 5, wherein the flow rate profile of at least the initial portion of the at least second fluid is delivered at a flow rate that varies between zero and the second predetermined flow rate over the specified intermediate time interval.

Clause 7. The method according to any of clauses 1 to 6, wherein injecting the initial portion of at least the second fluid comprises injecting the initial portion of at least the second fluid at an intermediate flow rate lower than the second predetermined flow rate over the specified intermediate time interval, wherein the specified intermediate time interval is selected to allow a residual portion of the first fluid to pass through a fluid line to the patient before beginning the step of injecting the remaining portion of the second fluid, wherein the specified intermediate time interval is based on one or more of system architecture; a capacitance of at least one of the first fluid reservoir and the second fluid reservoir, a length of the fluid line, a diameter of the fluid line, a volume of the fluid line, the length of a catheter, the diameter of the catheter, the volume of the catheter and any combination thereof.

Clause 8. The method according to any of clauses 1 to 6, wherein a volume of the initial portion of the second fluid of the fluid injection is determined by one or more of a volume capacity of a fluid line between the second fluid reservoir and the patient, a capacitance of at least one of the first fluid reservoir and the second fluid reservoir, and an injection system compliance.

Clause 9. The method according to any of clauses 1 to 8, further comprising inputting by a system user the flow rate profile of the second fluid based at least in part on one or more parameters selected from the group consisting of a table of injection protocols, first phase flow rate, second phase flow rate, transition flow rate, catheter volume, catheter diameter, catheter length, volume of the fluid line between the fluid reservoir and the patient, diameter of the fluid line, length of the fluid line, temperature of the first fluid, temperature of the second fluid, viscosity of the first fluid, viscosity of the second fluid, programmed volume of the first fluid to be delivered, and programmed volume of the second fluid to be delivered.

Clause 10. The method according to any of clauses 1 to 9, wherein the flow rate profile of the initial portion is selected to minimize flow rate deviations over the specified intermediate time interval.

Clause 11. The method according to any of clauses 1 to 10, wherein the flow rate profile of the initial portion is calculated based on the following equation:

$$Q(\text{transition})=Q(\text{programmed})-Q(\text{adjusted})$$

wherein Q(transition) is a desired flow rate profile at a transition between the first fluid to at least the second fluid;

Q(programmed) is a desired flow rate profile for the first fluid and at least the second fluid; and Q(adjusted) is a necessary adjustment of the flow rate of the second fluid so that Q(transition) at the transition between the first fluid and at least the second fluid a flow rate at a catheter tip is substantially similar to Q(programmed).

Clause 12. The method according to any of clauses 1 to 10, wherein the flow rate profile of the initial portion is calculated based on the following equation:

$$Q(t)=Q(p)-(C(1)-C(2))/t(t),$$

wherein Q(t) is the intermediate flow rate, Q(p) is the second predetermined flow rate, C(1) is a steady state system compliance during the first fluid phase, C(2) is a system compliance during the second fluid injection, and t(t) is a derived intermediate time for delivering the volume associated with the system compliance (C(2)).

Clause 13. The method according to clause 12, wherein the system compliance during the first fluid injection comprises a first compliance factor associated with one or more of the first fluid reservoir, a first fluid delivery mechanism, and a tubing set in operative fluid communication the first fluid reservoir, and the system compliance during the second fluid injection comprises a second compliance factor associated with one or more of the second fluid reservoir, a second fluid delivery mechanism, and a tubing set in operative communication the second fluid reservoir.

Clause 14. The method according to any of clauses 1 to 13, wherein the first fluid reservoir is a first syringe operatively connected to a first drive member of the fluid injector and at least the second fluid reservoir is at least a second syringe operatively connected to at least a second drive member of the fluid injector.

Clause 15. A fluid injector system for delivering a multi-phase fluid injection to a patient, the fluid injector system comprising: at least one first syringe configured to contain a first fluid of the multi-phase fluid injection, the first fluid having a first viscosity; at least one first drive member operatively connected with the at least one first syringe, the at least one first drive member being operable to dispense the first fluid of the multi-phase fluid injection; at least one second syringe configured to contain a second fluid of the multi-phase fluid injection, the second fluid having a second viscosity different from the first viscosity; at least one second drive member operatively connected with the at least one second syringe, the at least one second piston being operable to dispense the second fluid of the multi-phase fluid injection; a fluid line connected to the at least one first syringe and the at least one second syringe, and configured to deliver at least one of the first fluid of the multi-phase fluid injection from the at least one first syringe to the patient and the second fluid of the multi-phase fluid injection from the at least one second syringe to the patient; and a control device configured to control movement of the first drive member associated with the at least one first syringe and movement of the at least one second drive member associated with the at least one second syringe to control the delivery of the first fluid and the second fluid of the multi-phase fluid injection to the patient, wherein the control device is configured to control the first drive member to inject the first fluid at a first predetermined flow rate, to control the at least one second drive member to inject an initial portion of at least the second fluid of the fluid injection from the at least one second syringe at an intermediate flow rate profile different from a second predetermined flow rate for a specified intermediate time or intermediate fluid volume, and to inject a remaining portion of the second fluid at least equal to the second predetermined flow rate, wherein the second fluid has a second viscosity different from the first viscosity.

Clause 16. The fluid injector system according to clause 15, wherein the first viscosity is greater than the second viscosity.

Clause 17. The fluid injector system according to clause 15 or clause 16, wherein the first predetermined flow rate is substantially the same as the second predetermined flow rate.

Clause 18. The fluid injector system according to any of clauses 15 to 17, wherein the flow rate profile of at least the initial portion of the at least second fluid is delivered at a flow rate lower than the first predetermined flow rate, or wherein the flow rate profile of at least the initial portion of the at least second fluid is delivered at a flow rate that varies between zero and the first predetermined flow rate or the second predetermined flow rate over the specified intermediate time interval.

Clause 19. The fluid injector system according to any of clauses 15 to 18, wherein the control device is configured to time an injection of the initial portion of at least the second fluid comprises injecting the initial portion of at least the second fluid at an intermediate flow rate lower than the second predetermined flow rate over the specified intermediate time interval, wherein the specified intermediate time interval is selected to allow a residual portion of the first fluid to pass through a fluid line to the patient before beginning the step of injecting the remaining portion of the second fluid, wherein the specified intermediate time interval is based on system architecture; a capacitance of at least one of the first fluid reservoir and the second fluid reservoir, a length of the fluid line, a diameter of the fluid line, a volume of the fluid line, the length of a catheter, the diameter of the catheter, the volume of the catheter and any combination thereof.

Clause 20. The fluid injection system according to any of clauses 15 to 19, wherein the first fluid is selected from the group consisting of a contrast media, and a mixture of a specific ratio of the contrast media and saline, and wherein the second fluid is selected from the group consisting of saline and a mixture of a second specific ratio of the contrast media and saline.

Clause 21. The fluid injection system according to any of clauses 15 to 20, wherein the flow rate profile of the initial portion is calculated based on the following equation:

$$Q(\text{transition})=Q(\text{programmed})-Q(\text{adjusted})$$

wherein Q(transition) is an desired flow rate profile at a transition between the first fluid to at least the second fluid; Q(programmed) is a desired flow rate profile for the first fluid and at least the second fluid; and Q(adjusted) is a necessary adjustment of the flow rate of the second fluid so that Q(transition) at the transition between the first fluid and at least the second fluid a flow rate at a catheter tip is substantially similar to Q(programmed).

Clause 22. The fluid injection system according to any of clauses 15 to 20, wherein the flow rate profile of the initial portion is calculated based on the following equation:

$$Q(t)=Q(p)-(C(1)-C(2))/t(t),$$

wherein Q(t) is the intermediate flow rate, Q(p) is the second predetermined flow rate, C(1) is a system compliance during the first fluid injection, C(2) is a system compliance during the second fluid injection, and t(t) is a derived intermediate time for delivering the volume of the initial portion of the second fluid of the fluid injection.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only.

BRIEF DESCRIPTION OF THE DRAWINGS

FIG. 7A-7I illustrate several embodiments of flow profiles including transition phases by control of a motor speed of the fluid delivery system during a multi-phase injection;

FIG. 10 is an exemplary lookup table for deriving restriction and a steady state pressure for a multi-phase fluid injection;

DETAILED DESCRIPTION

Figure 1:
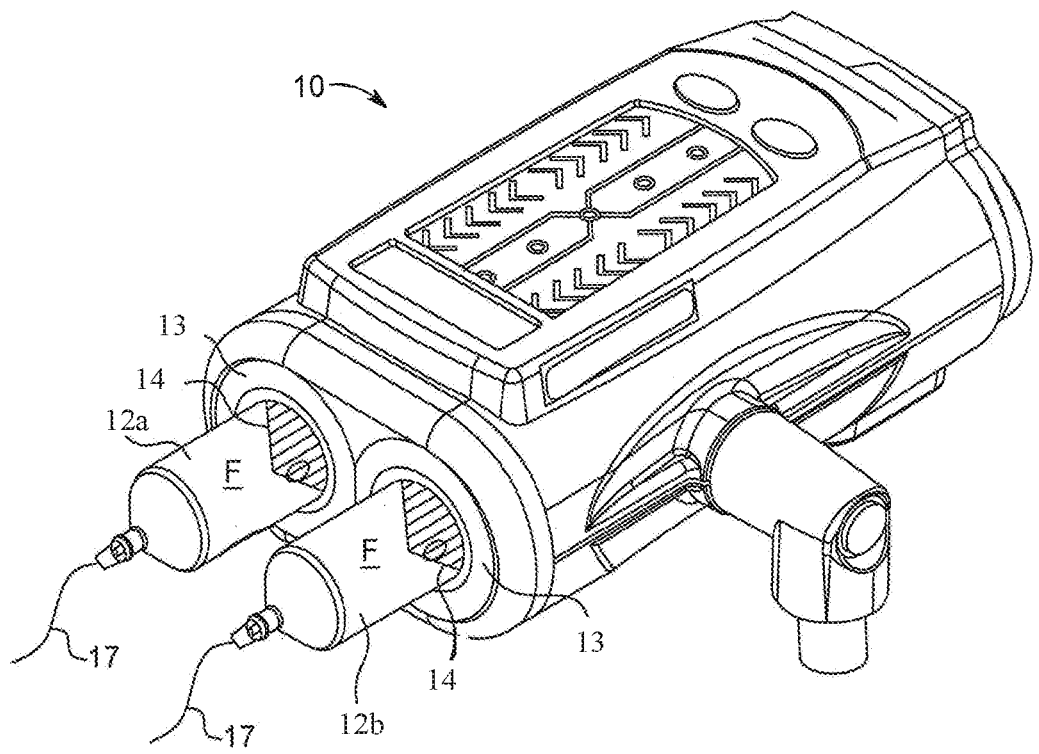
FIG. 1 is a perspective view of a fluid delivery system according to an example of the present disclosure.

As used in the specification and the claims, the singular form of "a", "an", and "the" include plural referents unless the context clearly dictates otherwise.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures.

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". The term "about" means a range of plus or minus ten percent of the stated value.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

The term "at least" means "greater than or equal to".

The term "includes" is synonymous with "comprises". "Comprises" includes "consisting of", and "consisting essentially of".

When used in relation to a syringe and/or a plunger, the term "proximal" refers to a portion of a syringe and/or a plunger nearest a fluid injector when a syringe and/or a plunger is oriented for connecting to a fluid injector. The term "distal" refers to a portion of a syringe and/or a plunger farthest away from a fluid injector when a syringe and/or a plunger is oriented for connecting to a fluid injector. The term "radial" refers to a direction in a cross-sectional plane normal to a longitudinal axis of a syringe, a plunger, and/or a piston extending between proximal and distal ends. The term "circumferential" refers to a direction around an inner or outer surface of a sidewall of a syringe, a plunger, and/or a piston. The term "axial" refers to a direction along a longitudinal axis of a syringe, a piston, and/or a piston extending between the proximal and distal ends. The term "open" when used to refer to a fluid delivery component means that the system is in fluid connection with an outlet, for example through a nozzle or the open end of a tubing component or catheter. In an open system, fluid flow may be constrained, for example by forcing a fluid through a small diameter fluid path where flow may be determined by physical parameters of the system and the fluid, such as tubing diameter, fluid path constrictions, applied pressure, viscosity, etc. The term "closed" when used to refer to a fluid delivery component means that the system is not in fluid connection with an outlet, for example where fluid flow is stopped by a valve, such as a stopcock, high crack pressure valve, pinch valve, and the like. As used herein the term "slack" means mechanical slack, including a clearance or lost motion in a mechanism caused by gaps between parts, compression of mechanical components under applied load (such as by applied pressure), deflection of mechanical components under applied load (such as by applied pressure), that results in a delay of pressurized delivery of a fluid from a fluid injection after application of force.

It is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the examples disclosed herein are not to be considered as limiting.

Characterizing an impedance of a fluid delivery system to minimize a difference between desired and actual fluid delivery system performance requires consideration how energy from an energy source is used in or moves through the system. The energy output or loss from the fluid delivery system may be in the form of heat losses through frictional forces or of work done on the fluid delivery system. For example, some of the energy carried by the pressurized fluid as it is delivered under pressure through a catheter is lost through resistive, frictional, or dissipative heating of the fluid. Additionally, pressurized delivery of fluid can also increase the potential energy of the system in terms of an increase in overall volume of system components or compressive forces on system components, as discussed herein. Furthermore, the kinetic energy of pressurized fluid moving through the fluid delivery system can affect the overall performance of the fluid delivery system. For example, inertial forces of moving contrast material and expansion of the containers and/or tubing associated with the system may cause a phase lag between movement of the syringe plunger within the injector syringe and movement of contrast material out of the catheter and into the patient.

Due to high injection pressures, which may be on the order of 1,200 psi in some angiographic procedures, there may be an expansion, deflection, or compression of various components of the fluid delivery system, such as the syringes, tubing connected to the patient, and components of the fluid injector, such that there may be a volume of fluid in the syringe and tubing in excess of the desired quantity selected to be delivered in the injection procedure. Such increase in the quantity of fluid occurs due to system capacitance. Total system capacitance (also referred to as compliance or elasticity) represents the amount of fluid (i.e., change in volume, such as excess volume) that is captured in the swelling of the components of the fluid delivery system. In general, capacitance is directly correlative to injection pressure and directly correlative to pressurized fluid volume of contrast medium and saline in the syringes, for example, the greater the volume the greater the inner surface area of the syringe that may be expanded. In other words, capacitance increases with an increase in injection pressure and an increase in volume of fluid in the syringes. Total system capacitance is inherent to each fluid delivery system and depends on a plurality of factors beyond pressure and volume of fluid remaining in the system, including, without limitation, injector construction, mechanical properties of materials used to construct the syringe, plunger, pressure jacket surrounding the syringe, and fluid lines delivering the fluid to the patient, size of the syringe, plunger, pressure jacket, diameter of tubing or other orifices through which the fluid must pass under pressure, and fluid properties, such as temperature, viscosity, and density.

In some fluid delivery systems, such as fluid delivery systems having two or more syringes each independently driven by a piston of the fluid injector, where two or more different fluids having different properties, such as viscosities, temperature, and/or density, are independently stored in the two or more syringes, fluid flow rates may fluctuate during delivery procedures having multiple phases where a delivery of a first fluid having first properties is followed by a delivery of a second fluid having second properties different from the first properties. In such delivery procedures, an overall fluid flow rate at a transition between the delivery of the first fluid and the delivery of the second fluid may vary or fluctuate due to differences in stored pressures in the fluid delivery system and fluid flow dynamics between the two fluids. For example, viscous fluids may require higher applied pressures to achieve comparable fluid flow rates relative to less viscous fluids. Accordingly, a first delivery phase using the first fluid having a relatively high viscosity, such as contrast, may require a higher applied pressure to achieve a target flow rate than a second delivery phase using the second fluid having a relatively low viscosity compared to the first fluid, such as saline. During injections where a first phase of an injection with the first fluid is followed by a second phase of the injection with the second fluid, this difference in pressure necessary to achieve target flow rates for the two different fluids may result in undesired fluctuations in the overall flow rate during the transition between the first phrase and the second phase.

Figure 8:
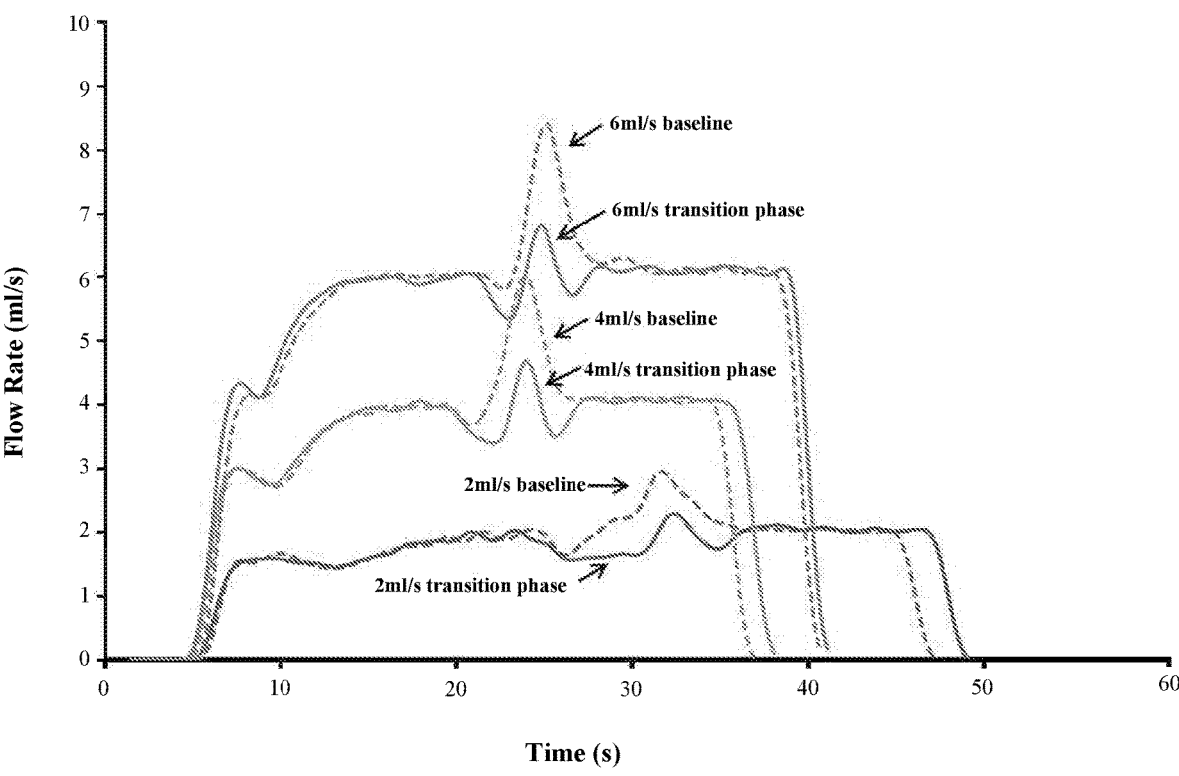
FIG. 8 is a chart comparing a measured flow rate of a multi-phase fluid injection at a phase transition to a measured flow rate of the multi-phase injection at a transition phase.

In closed systems, where fluid flow from the at least one syringe may be closed by a stopcock or other flow control member, equalization of syringe capacitance between multiple syringes is prevented and capacitance is stored in the closed syringe, thereby potentially affecting the flow rates of the subsequent fluid delivery from that syringe. In addition, residual first fluid in a fluid line must be pushed out of the line by the second fluid, which in certain situations may require a higher pressure than a desired pressure until the first fluid is purged. At the transition between the delivery of the first fluid to the delivery of the second fluid, the higher-than-desired pressure may result in an increase in flow rate of the second fluid as the last of the first fluid exits the fluid line, particularly in injections where the first fluid is more viscous than the second fluid. For example, as illustrated in FIG. 8, the dotted lines illustrates the fluid flow rate fluctuations observed at the transition from a highly viscous fluid for several desired programmed flow rates, such as a contrast media which can range from 2.0 to 30.0 cP (at 20° C.), to a lower viscosity fluid, such as saline having a viscosity of 1.0 to 1.5 cP (at 20° C.). These undesired fluctuations of flow rate may result, for example, in variations and inaccuracies of delivery of fluid volumes and potentially problems with bolus consistency and, ultimately, image quality when contrast agents are being injected. Accordingly, there is a need in the art for improved control of fluid delivery from a fluid injector. There is a further need for improved systems and methods for limiting fluid flow fluctuations in fluid injections having at least one transition between the delivery of fluids having different physical properties.

According to various embodiments, the present disclosure provides methods for delivering a multi-phase fluid injection to a patient via a fluid injector, such as delivering a fluid injection protocol with an imaging contrast agent and a saline flush, including defined mixtures of contrast and saline. The fluid injector may include two or more fluid reservoirs, such as reservoirs selected from the group consisting of a syringe, a compressible bag, a peristaltic pump, and various combinations thereof, such as at least one syringe and at least one peristaltic pump. In specific embodiments, the fluid injector may include a first syringe and a second syringe. In other embodiments, the fluid injector may include a first syringe, a second syringe, and a third syringe. In certain embodiments, the syringe may be a rolling diaphragm type syringe. The method may include injecting a first fluid of the fluid injection from at least a first fluid reservoir where the first fluid having a first viscosity and where the first fluid is delivered to the patient at a first predetermined flow rate, which may be a constant flow rate or a ramped flow rate. In certain embodiments, the first fluid may be a contrast agent, a saline, or a defined mixture of contrast agent and saline. In specific embodiments, the first fluid may be a contrast agent or a defined mixture of contrast agent and saline.

The method may further include injecting an initial portion of at least a second fluid of the fluid injection from at least a second fluid reservoir at a flow rate selected to minimize fluid flow fluctuations at the transition, as describe herein, where the second fluid has a second viscosity which is different from the first viscosity of the first fluid. In certain embodiments, the first fluid may have a viscosity that is greater than the viscosity of the second fluid, for example where the first fluid is a contrast agent and the second fluid is saline. In other embodiments, the first fluid may have a viscosity that is less than the viscosity of the second fluid. In still other embodiments, the first fluid may have a viscosity that is substantially the same as the viscosity of the second fluid. Viscosity of the fluid may vary according to the amount of a dissolved solute per volume of solvent (i.e., a fluid with a higher concentration of dissolved solute will be more viscous than a fluid with a lower concentration of the dissolved solute). According to the various embodiments herein the initial portion of the second fluid may be delivered to the patient with a flow rate profile different from a second predetermined flow rate for a specified intermediate time interval, while the remaining volume of the second fluid (i.e., after the initial portion) may be delivered to the patient at the second predetermined flow rate. In various embodiments, the second predetermined flow rate is substantially the same as the first predetermined flow rate. As used herein, the term "substantially the same" when referring to a second value means ranging from −10% to 10% (i.e., ranging from 10% less than to 10% greater than) of the first value. In specific embodiments, the flow rate profile of the initial portion of the second fluid include a flow rate lower than the first predetermined flow rate. For example, the flow rate of the initial portion of the second fluid may be from 0% to 100% of that of the second predetermined flow rate or of that of the first predetermined rate.

In other embodiments, the flow rate of the initial portion of the at least second fluid may be delivered at a flow rate that varies over the specified intermediate time interval. For example, in one embodiment, the intermediate flow rate may vary by slowly ramping from 0 mL/sec up to the second predetermined flow rate over the specified intermediate time interval. In other embodiments, the intermediate flow rate may vary by slowly ramping from 0 mL/sec up to a transitional flow rate over the specified intermediate time interval, where the transitional flow rate is less than at least one of the first predetermined flow rate and the second predetermined flow rate. According to other embodiments where the intermediate flow rate comprises a ramp from 0 mL/sec to at least one of the first predetermined flow rate, the second predetermined flow rate, and the transitional flow rate, the intermediate time may start during the injection of the first fluid at the first predetermined flow rate and continue on past the end of the injection of the first fluid to before the injection of the second fluid at the second predetermined flow rate (i.e., at the end of the specified intermediate time).

In other embodiment, the intermediate flow rate may be input by a system user the flow rate profile of the second fluid based at least in part on one or more parameters selected from the group consisting of a of a table of injection protocols, first phase flow rate, second phase flow rate, transition flow rate, catheter volume, catheter diameter, catheter length, volume of the fluid line between the fluid reservoir and the patient, diameter of the fluid line, length of the fluid line, temperature of the first fluid, temperature of the second fluid, viscosity of the first fluid, viscosity of the second fluid, programmed volume of the first fluid to be delivered, and programmed volume of the second fluid to be delivered. For example, the intermediate flow rate may be manually input by a system user base at least in part on one or more predetermined factors. Examples of predetermined factors may be provided from or derived from a predetermined table of factors, such as one or more tables containing one or more of a listing of pressures, volumes, flowrates, formula equations, and combinations of any thereof which can be reviewed or utilized to determine or calculate the intermediate flow rate. In certain embodiments, the user may recall the one or more tables from a processor memory and/or display the one or more tables on a screen associated with the injector. In another embodiment, the injector processor may automatically recall the tables from memory and calculate a suggested intermediate flow rate based on various injection parameters. Other potential flow profiles for the first and/or second fluid phase are described in detail in FIGS. 7A-7I.

In various embodiments, injecting the initial portion of at least the second fluid may include injecting the initial portion of at least the second fluid at an intermediate flow rate lower than the second predetermined flow rate over the specified intermediate time interval. In certain embodiments, the specified intermediate time interval is selected to allow a residual portion of the first fluid to pass through a fluid line and into the patient before beginning the step of injecting the remaining portion of the second fluid, for example at the second predetermined flow rate. The specified intermediate time interval maybe based on one or more different factors. For example, the specified intermediate time interval may be selected at least partially base on features of the fluid injector system architecture. For example, the fluid injector system architecture may include features of the drive system of a first pressurization feature and/or a second pressurization feature, such as a motor, gearing, and other mechanical features of a first and/or a second drive system associated with a first pressurization feature and/or a second pressurization feature, respectively Examples of such pressurization features include, but are not limited to, features of a motorized piston based drive members for reversibly moving one or more plunger of one or more syringe, features of a motorized peristaltic pump based drive system, and mechanical features of a clam-shell compression feature for a compressible bag based system. Upon pressurization of various mechanical components, compression of the mechanical components may result in an amount of slack where the pressurization force is not immediately converted to fluid flow due to compression of and/or strain on mechanical components, such as gearing and drive components of the fluid injector that apply the pressure. Another factor may include a capacitance of at least one of system architecture, a capacitance of at least one of the first fluid reservoir and the second fluid reservoir, pressure and/or flow rate of the first fluid, pressure and/or flow rate of the second fluid, a length of the fluid line, a diameter of the fluid line, a volume of the fluid line, the length of a catheter, the diameter of the catheter, the volume of the catheter and any combination thereof. Other factors may include expansion of the fluid reservoirs, such as syringes and tubing such that there may be an increased volume of fluid in the syringe and tubing in excess of the desired quantity selected to be delivered in the injection procedure. Such increase in the volume of fluid in the fluid reservoir or tubing occurs due to increased system capacitance (i.e., increased fluid volume capacity). Total system capacitance is inherent to each fluid delivery system and depends on a plurality of factors beyond pressure and volume of fluid remaining in the system, including, without limitation, fluid properties (such as viscosity, temperature, etc.), injector construction, mechanical properties of materials used to construct the syringe or reservoir, plunger, pressure jacket surrounding the syringe, fluid lines delivering the fluid to the patient, size of the syringe, plunger, pressure jacket, diameter of tubing or other orifices through which the fluid must pass under pressure, and fluid properties, such as temperature, viscosity, and density. System capacitance may result in discrepancies between programmed fluid volume delivery and actual volume delivery. For example, when beginning a pressurized fluid delivery, initial pressurization may result in swelling of system components under fluidized pressure and/or compression of mechanical components under force, rather than delivery of a corresponding fluid volume to a patient.

According to various embodiments, the first fluid may be a contrast media, such as a CT contrast agent, a CV contrast agent, an MRI contrast agent, a PET radioactive contrast agent, an ultrasound contrast, or combinations of any thereof. In other embodiments, the first fluid may be a dual flow mixture of a first specified ratio of a contrast agent, as described herein, and the second fluid, such as saline or other flushing fluid, such as Ringer's lactate. In still other embodiments, mixtures of three or more fluids are contemplated, wherein the fluids comprise a specified ratio of at least one contrast agent, saline, and a third medical fluid (such as a second contrast agent or other medical fluid). According to various embodiments, the second fluid may be a medical flushing agent (such as saline or water) or a mixture of a contrast agent and the flushing agent, wherein the mixture has a second specified ratio of the contrast and the flushing agent that is different than the first specified ratio. According to certain embodiment, the first specified ratio of contrast to flushing fluid and/or the second specified ratio of contrast to flushing may vary over the course of an injection protocol. For example, in a dual flow contrast injection of the first fluid at a first specified ratio, the injected first fluid may start at an 80:20 ratio of contrast to saline and ramp to a 20:80 ratio of contrast to saline over at least a portion of the injection time of the first fluid. In another example, the second fluid may include a dual flow ramp at the second specified ratio, where the injected second fluid is injected over the remaining time and may start at a 10:90 specified ratio of contrast agent to saline and ramp to a 0:100 specified ratio of contrast to saline. According to other embodiments, the initial portion of the second fluid may be injected as a specified dual flow ratio of the first fluid and the second fluid over the specified intermediate time. In still other embodiments, the initial portion of the second fluid may be injected at a ramp from a specified intermediate dual flow ratio of the first fluid and the second fluid to a second specified intermediate dual flow ratio of the first fluid and the second fluid over the specified intermediate time. One of skill in the art, reading the current disclosure, will understand that the ratios of the first fluid and the second fluid that are used in the dual flow portions of the injections may be any ratio of the first and second fluid, and the specific ratios detailed herein are for reference only. All other potential ratios are within the scope of the invention. In other embodiments, the volume of the initial portion of the second fluid of the fluid injection may be determined by one or more of a volume capacity of a fluid line between the second fluid reservoir and the patient, a capacitance of at least one of the first fluid reservoir and the second fluid reservoir, and an injection system compliance According to various embodiments herein, the flow rate profile of the initial portion is selected to minimize flow rate deviations over the specified intermediate time interval. For example, as illustrated in FIG. 8, fluid transitions from a fluid having a first viscosity to a fluid having a second, different viscosity may result in fluid flow fluctuations or other deviations from the intended fluid flow rate over the specified intermediate time interval. For examples, in certain embodiments when the fluid flow transitions from a more viscous first fluid to a less viscous second fluid, flow fluctuations may be observed since the second fluid must be pressurized to a greater pressure than necessary to push the remaining first fluid from the fluid path into the patient at the first predetermined flow rate. As soon as the last of the more viscous fluid exits the fluid path, the increased pressure on the second less viscous fluid may result in sudden fluctuations of fluid velocity of the second fluid exiting the fluid path. By appropriate selection of a flow rate for the initial portion of the second fluid, for example where the flow rate is less than the first predetermined flow rate and the second predetermined flow rate, as described herein, the sudden increase in fluid velocity of the second fluid exiting the fluid path may be reduced, minimized, or substantially eliminated.

According to various embodiments, the flow rate and/or the flow rate profile of the initial portion of the second fluid may be calculated using an equation that takes into account one or more of various factors described herein to provide a calculated transition flow rate selected to minimize any fluctuations or deviations in the fluid flow rate of fluid entering the patient at the transition from the first fluid to the second fluid. According to certain embodiments, the flow rate and/or flow rate profile of the initial portion based on equation (1):

$$Q(\text{transition}) = Q(\text{programmed}) - Q(\text{adjusted}) \qquad (1)$$

According to equation (1), (transition) is a desired flow rate profile over a transition between the first fluid to at least the second fluid by adjusting the drive member movement (speed over distance) to control the fluid flow out of the catheter tip; Q(programmed) is a desired flow rate profile for the at least the second fluid; and Q(adjusted) is a necessary adjustment of the flow rate of the second fluid so that Q(transition) at the transition between the first fluid and at least the second fluid results in a fluid flow rate from the catheter that is substantially similar to Q(programmed). According to specific embodiments, the intermediate time may be substantially question to the time that it takes for the remaining amount of the first fluid to be delivered out of the fluid line, for example by dividing the volume of the fluid line and catheter by the programmed flow rate. To avoid fluctuations in the fluid flow, the equation values are selected so that Q(transition) results in a flow rate substantially similar to Q(programmed).

According to other embodiments, the flow rate and/or flow rate profile of the initial portion based on equation (2):

$$Q(t) = Q(p) - (C(1) - C(2))/t(t) \qquad (2)$$

According to equation (2), Q(t) is the intermediate flow rate, Q(p) is the second predetermined flow rate, C(1) is a steady state system compliance during the first fluid phase, C(2) is a system compliance during the second fluid injection, and t(t) is a derived time for delivering the volume associated with the system compliance (C(2)). According to various embodiments, the system compliance during the first fluid injection comprises a first compliance factor associated with one or more of the first fluid reservoir, a first fluid delivery mechanism, and a tubing set in operative fluid communication the first fluid reservoir, and the system compliance during the second fluid injection comprises a second compliance factor associated with one or more of the second fluid reservoir, a second fluid delivery mechanism, and a tubing set in operative communication the second fluid reservoir. The system compliance of the first reservoir and/or the at least the second reservoir may be measured, for example using a flow sensor in the fluid path between the reservoir(s) and the catheter. Alternatively the one or both of the system compliance of the first reservoir and/or the at least the second reservoir may be may be predicted based on factors of the fluid injector, the first or second fluid reservoir, and the first or second fluid, respectively. According to these embodiments, the system compliance during the first fluid injection comprises a first compliance factor associated with one or more of the first fluid reservoir, a first fluid delivery mechanism, and a tubing set and catheter in operative fluid communication the first fluid reservoir, and the system compliance during the second fluid injection comprises a second compliance factor associated with one or more of the second fluid reservoir, a second fluid delivery mechanism, and a tubing set and catheter in operative communication the second fluid reservoir, including pressure applied to each fluid reservoir and volume of fluid remaining in each fluid reservoir. Alternatively, the capacitance of a fluid injector and associated components may be at least partially measured optically, for example by measuring swelling of a fluid reservoir, compression of mechanical components and plunger features, and deflection of system components under pressure, by comparing the relaxed state to the pressurized state.

As described herein, in specific embodiments of the fluid injector and methods, the first fluid reservoir may be a first syringe operatively connected to a first drive member of the fluid injector and at least the second fluid reservoir may be at least a second syringe operatively connected to at least a second drive member of the fluid injector.

For example, according to certain embodiments, fluid injector system for delivering a multi-phase fluid injection to a patient may comprise at least one first syringe and at least one second syringe. The at least one first syringe may be configured to contain a first fluid of the multi-phase fluid injection where the first fluid has a first viscosity and the injector may include at least one first drive member operatively connected with the at least one first syringe where the at least one first drive member is operable to dispense the first fluid of the multi-phase fluid injection. The at least one second syringe may be configured to contain a second fluid of the multi-phase fluid injection where the second fluid has a second viscosity different from the first viscosity and the injector may include at least one second drive member operatively connected with the at least one second syringe where the at least one second piston being operable to dispense the second fluid of the multi-phase fluid injection. The injector may further include a fluid line that is fluidly connected to the at least one first syringe and the at least one second syringe, and configured to deliver at least one of the first fluid of the multi-phase fluid injection from the at least one first syringe to the patient and the second fluid of the multi-phase fluid injection from the at least one second syringe to the patient. In various embodiments, the injector system may include a third syringe, and in other embodiments may include other fluid delivery mechanisms such as one or more peristaltic pumps and/or one or more compressible reservoirs. According to various embodiments, the first syringe and the at least second syringe may be part of a closed system, wherein the first syringe and the at least second syringe are configured to be independently isolated from the remainder of the fluid path, for example by a valve, stopcock, or other feature that can selectively and reversibly isolate one or both of the first and at least second syringe from the fluid path. According to other embodiments, the first syringe and/or the at least second syringe may be part of an open system, wherein one or both of the first syringe and the at least second syringe are configured to be in fluid communication with the fluid path during the injection procedure. Various embodiments of the fluid injector may include a control device configured to control movement of the first drive member associated with the at least one first syringe and movement of the at least one second drive member associated with the at least one second syringe to control the delivery of the first fluid and the second fluid of the multi-phase fluid injection to the patient. For example, the control device may be configured to control the first drive member to inject the first fluid at a first predetermined flow rate, to control the at least one second drive member to inject an initial portion of at least the second fluid of the fluid injection from the at least one second syringe at an intermediate flow rate profile different from a second predetermined flow rate for a specified intermediate time, and to inject a remaining portion of the second fluid at least equal to the second predetermined flow rate, wherein the second fluid has a second viscosity different from the first viscosity. According to various embodiments, the control device, such as a processor, may be configured to operate the fluid injector to independently open and close the fluid connectivity of the first and/or second syringe with the remainder of the fluid path.

With reference to FIG. 1, a fluid injector 10 (hereinafter referred to as "injector 10"), such as an automated or powered fluid injector, is adapted to interface with and actuate one or more syringes 12 (hereinafter referred to as "syringe 12"), which may be filed with a fluid F, such as contrast media, saline solution, or any desired medical fluid. The injector 10 may be used during a medical procedure to inject the medical fluid into the body of a patient by driving a plunger 14 of each syringe 12 with a drive member, such as piston 19 (shown in FIG. 2), such as linear actuator or a piston element. The injector 10 may be a multi-syringe injector having two, three or more syringes, wherein the several syringes 12 may be oriented in a side-by-side or other relationship and may be separately actuated by respective drive members/pistons 16 associated with the injector 10. In examples with two or more syringes, for example, arranged in a side-by-side or other relationship and filled with two different fluids, the injector 10 may be configured to deliver fluid from one or both of the syringes 12, sequentially or concurrently. According to one embodiment, the fluid injector 10 may be a dual head injector having two syringes 12a and 12b, a first syringe 12a for delivering a contrast media or other medical fluid and a second syringe 12b for delivering saline or other medically approved flushing agent to flush the contrast media to the patient. In other embodiments, the fluid injector 10 may have three syringes 12, a first and second syringe for delivering one or two different contrast media or other medical fluid and a third syringe for delivering saline or other medically approved flushing agent to flush the contrast media to the patient. According to various embodiments, the fluid injector 10 may be configured to deliver the contrast and saline separately (e.g., delivering a specific volume saline over a specific time followed by delivering a specific volume of contrast over a specific time, followed by a second volume of saline over a specified time to flush the contrast media from the tubing into the patient). According to various embodiments, the fluid injector 10 may be configured to deliver the contrast and saline separately or as a mixture (e.g., delivering a specific volume saline over a specific time followed by delivering a specific volume of contrast or a specified ratio of contrast and saline (i.e., in a "dual flow"

process) over a specific time, followed by a second volume of saline over a specified time to flush the contrast media from the tubing into the patient). A technician may program a specific injection protocol into the injector (or use a pre-written protocol) to deliver the desired volumes of saline, contrast, specific ratios of contrast and saline mixtures, etc., at a desired flow rate, time, and volume for each solution. The fluid injector 10 may have at least one bulk fluid source (not shown) for filling the syringes 12a,b with fluid and in certain embodiments, the fluid injector 10 may have a plurality of bulk fluid source, one for each of the plurality of syringes, for filling each of the plurality of syringes with the desired fluid.

A fluid path set 17 may be in fluid communication with each syringe 12 to place each syringe in fluid communication with a catheter for delivering the fluid F from each syringes 12 to a catheter (not shown) inserted into a patient at a vascular access site. In certain embodiments, fluid flow from the one or more syringes 12 may be regulated by a fluid control module (not shown) that operates various valves, stopcocks, and flow regulating structures to regulate the delivery of the saline solution and contrast to the patient based on user selected injection parameters, such as injection flow rate, duration, total injection volume, and ratio of fluids from the syringes 12, including specific ratios of each fluid in a dual flow injection protocol.

Figure 2:
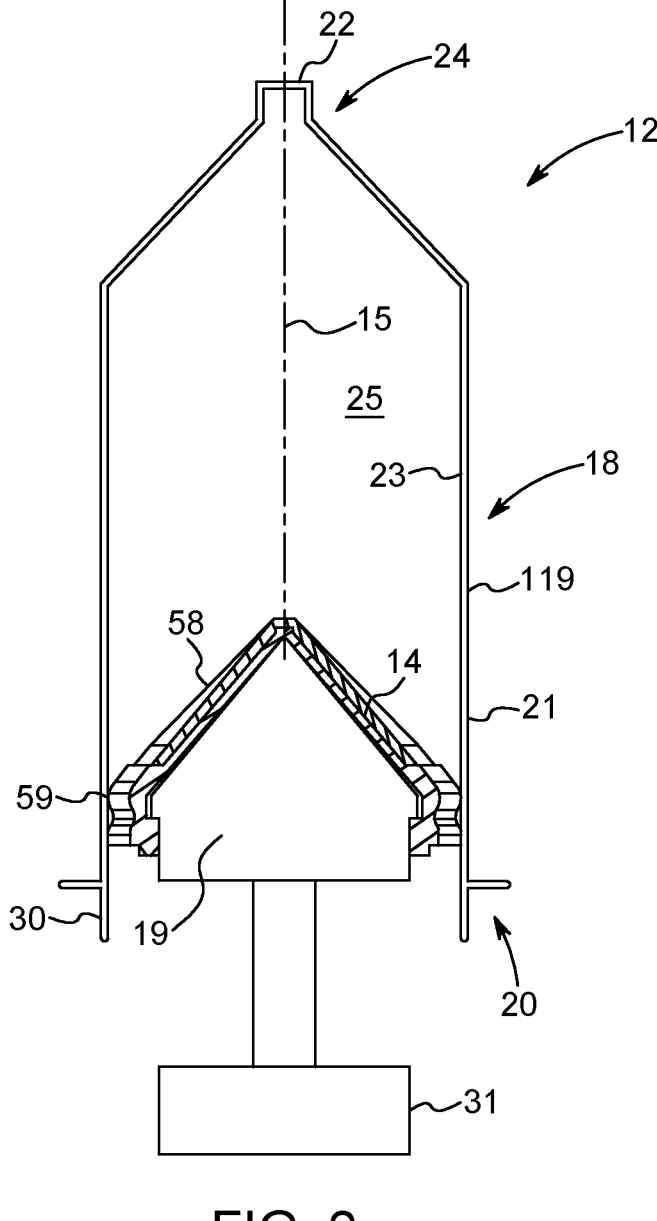
FIG. 2 is a cross-sectional view of a syringe configured for use with the fluid delivery system of FIG. 1.

With reference to FIG. 2, the drive member 19, such as a reciprocally driven piston moved by a motor 31, may be configured to extend into and from the respective syringe port 13 through an opening in the front end of the injector housing. In fluid injector embodiments comprising a plurality of syringes, a separate drive member/piston 19 may be provided for each syringe 12. Each drive member/piston 19 is configured to impart a motive force to at least a portion of the syringe 12, such as the plunger 14 or a distal end of a rolling diaphragm syringe (for example, as described in PCT/US2017/056747; WO 2016/172467; and WO 2015/164783, the disclosures of which are incorporated herein by this reference). The drive member or piston 19 may be reciprocally operable via electro-mechanical drive components such as a ball screw shaft driven by the motor 31, a voice coil actuator, a rack-and-pinion gear drive, a linear motor, a linear actuator, and the like. The motor 31 may be an electric motor.

Examples of suitable front-loading fluid injectors 10 are disclosed in U.S. Pat. Nos. 5,383,858; 7,553,294; 7,666,169; 9,173,995; 9,199,033; and 9,474,857; and in PCT Application Publication No. WO 2016/191485 and WO 2016/112163, the disclosures of which are incorporated by reference in their entirety.

Having described the general structure and function of specific embodiments of the fluid injector 10, an embodiment of syringe 12 configured for use with the injector 10 will now be described with reference to FIG. 2. The syringe 12 generally has a cylindrical syringe barrel 18 formed from glass, metal, or a suitable medical-grade plastic. The barrel 18 has a proximal end 20 and a distal end 24, with a sidewall 119 extending therebetween along a length of a longitudinal axis 15 extending through a center of the barrel 18. In some examples, the distal end 24 may have a conical shape that narrows in a distal direction from the cylindrical barrel 18. A nozzle 22 extends from the distal end 24. The barrel 18 has an outer surface 21 and an inner surface 23 with an interior volume 25 configured for receiving the fluid therein. The proximal end 20 of the barrel 18 may be sealed with the plunger 14 that is reciprocally movable through the barrel 18 by reciprocal movement of the corresponding piston 19 or drive member. The plunger 14 forms a liquid-tight seal against the inner surface 23 of the barrel 18 as the plunger 14 is advanced moved through the barrel 18.

With continued reference to FIG. 2, the proximal end 20 of the syringe 12 is sized and adapted for being removably inserted in a syringe port 13 of an injector 10 (shown in FIG. 1). In some examples, the proximal end 20 of the syringe 12 defines an insertion section 30 that is configured to be removably inserted into the syringe port 13 of the injector 10 while the remaining portion of the syringe 12 remains outside of the syringe port 13.

The syringe 12 may be made of any suitable medical-grade plastic or polymeric material, desirably a clear or substantially translucent plastic material. The material of the syringe 12 is desirably selected to meet the required tensile and planar stress requirements, water vapor transmission, and chemical/biological compatibility. Exemplary syringes suitable for use with the injector 10 depicted in FIG. 1 are described in U.S. Pat. Nos. 5,383,858; 6,322,535; 6,652,489; 9,173,995; and 9,199,033, the disclosures of which are all incorporated by reference in their entirety.

Figure 3:
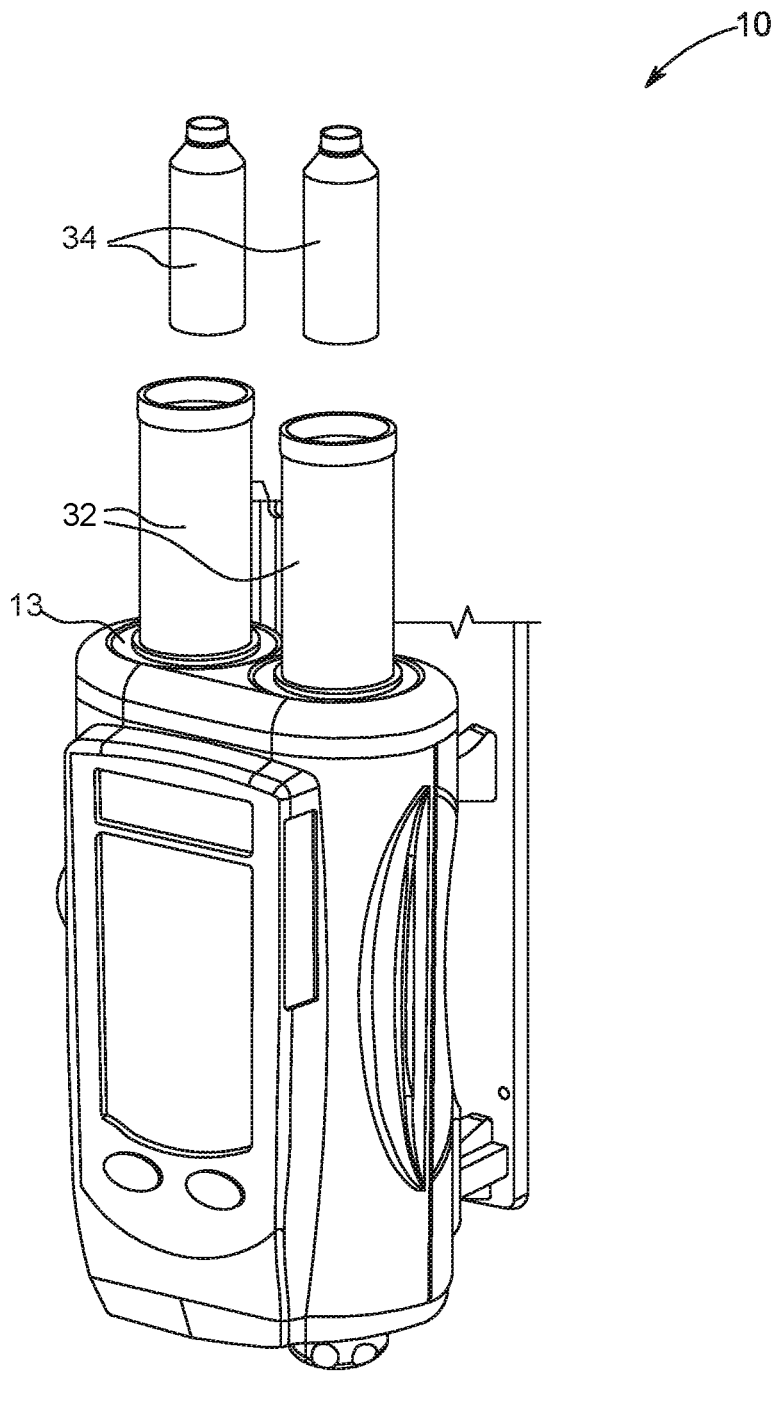
FIG. 3 is a perspective view of a fluid delivery system according to another example of the present disclosure.

In some examples, such as shown in FIG. 3, the injector 10 may be configured for receiving and retaining a pressure jacket 32 within each syringe port 13 of the injector 10. While FIGS. 1 and 3 illustrate fluid injectors 10 with two syringe ports 13, which for the injector 10 shown in FIG. 3 each having a corresponding pressure jacket 32, other examples of the fluid injector 10 may include a single syringe port 13 and optionally, a corresponding pressure jacket 32 or more than two syringe ports 13 with an optional corresponding number of pressure jackets 32. In embodiments comprising pressure jackets, each pressure jacket 32 may be configured to receive a syringe, such as a syringe for an angiographic (CV) procedure, or a rolling diaphragm syringe 34 (suitable examples of which are described in described in PCT/US2017/056747; WO 2016/172467; and WO 2015/164783). A fluid path set, similar to the fluid path set 17 shown in FIG. 1, may be fluidly connected with a discharge end of each rolling diaphragm syringe 34 for delivering fluid from the syringes 34 through tubing connected to a catheter, needle, or other fluid delivery connection (not shown) inserted into a patient at a vascular access site. According to various embodiments, the syringe 12 or 34 may be a pre-filled syringe, i.e., the syringe may be prefilled with a medical fluid, such as a contrast agent or saline, when provided by the syringe manufacturer. According to certain embodiments, the pre-filled syringe may be required to be spiked or otherwise punctured at the discharge end prior to an injection procedure to allow fluid to be expelled from the syringe into a fluid line to the patient, as described herein.

Figure 4:
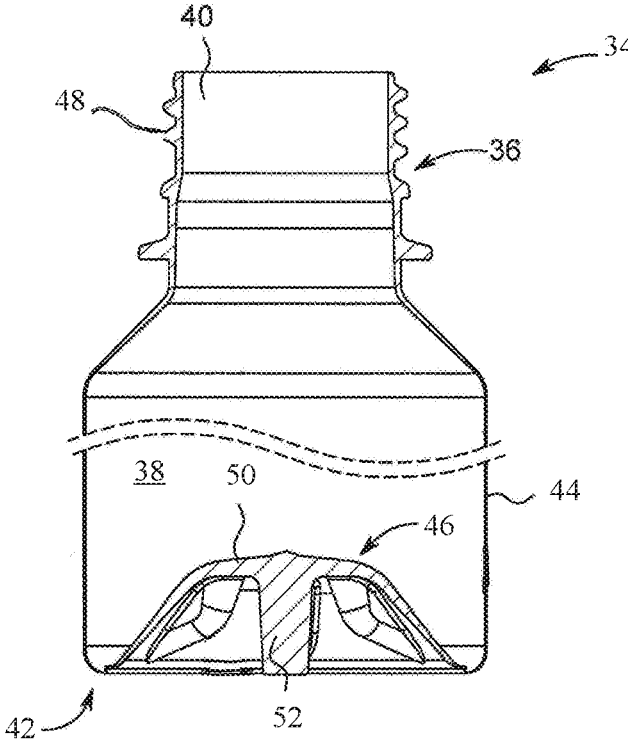
FIG. 4 is a cross-sectional view of a syringe configured for use with the fluid delivery system of FIG. 3.

With reference to FIG. 4, the rolling diaphragm syringe 34 generally includes a hollow body 36 defining an interior volume 38. The body 36 has a forward or distal end 40, a rearward or proximal end 42, and a flexible sidewall 44 extending therebetween. The proximal end 42 may be configured to act as piston to pressurize the syringe interior to draw in or expel fluid therefrom, as described herein. The sidewall 44 of the rolling diaphragm syringe 34 defines a soft, pliable or flexible, yet self-supporting body that is configured to roll upon itself, as a "rolling diaphragm", under the action of the a drive member or piston of the fluid injector 10. The drive member/piston 19 may be configured to releasably engage a drive member engagement portion 52 at the proximal end 42 of the rolling diaphragm syringe 34 (examples of which are described in PCT/US2017/056747). In operation, the sidewall 44 is configured to roll such that its outer surface is folded and inverted in a radially inward direction as the drive member/piston 19 moves the proximal end 42 in a distal direction and unrolled and unfolded in the opposite manner in a radially outward direction as the drive member/piston 19 retract the proximal end 42 in a proximal direction.

With continued reference to FIG. 4, the rearward or proximal portion of the sidewall 44 connects to a closed end wall 46, and a forward or distal portion of the sidewall 44 defines a discharge neck 48 opposite the closed end wall 46. The closed end wall 46 may have a concave shape to facilitate the initiation of the inversion or rolling of the sidewall 44, enhance mechanical strength of the closed end wall 46, and/or to provide a receiving pocket to receive a distal end of drive member/piston 19. For example, the closed end wall 46 may define a receiving end pocket for interfacing directly with a similarly-shaped distal end of the drive member/piston 19. In some examples, at least a portion of the drive member/piston 19 may be shaped to substantially match the shape of the closed end wall 46 or, alternatively, pressure from the drive member/piston 19 as it is moved distally may conform the end wall 46 to substantially match the shape of at least a portion of the drive member/piston 19.

The end wall 46 may have a central portion 50 having a substantially dome-shaped structure and a drive member engagement portion 52 extending proximally from the central portion 50. The drive member engagement portion 52 is configured for releasably interacting with a corresponding engagement mechanism on the drive member/piston 19 of the fluid injector 10, for example as the drive member/piston is retracted. The rolling diaphragm syringe 34 may be made of any suitable medical-grade plastic or polymeric material, desirably a clear or substantially translucent plastic material. The material of the rolling diaphragm syringe 34 is desirably selected to meet the required tensile and planar stress requirements, water vapor transmission, and chemical/biological compatibility.

Figure 5:
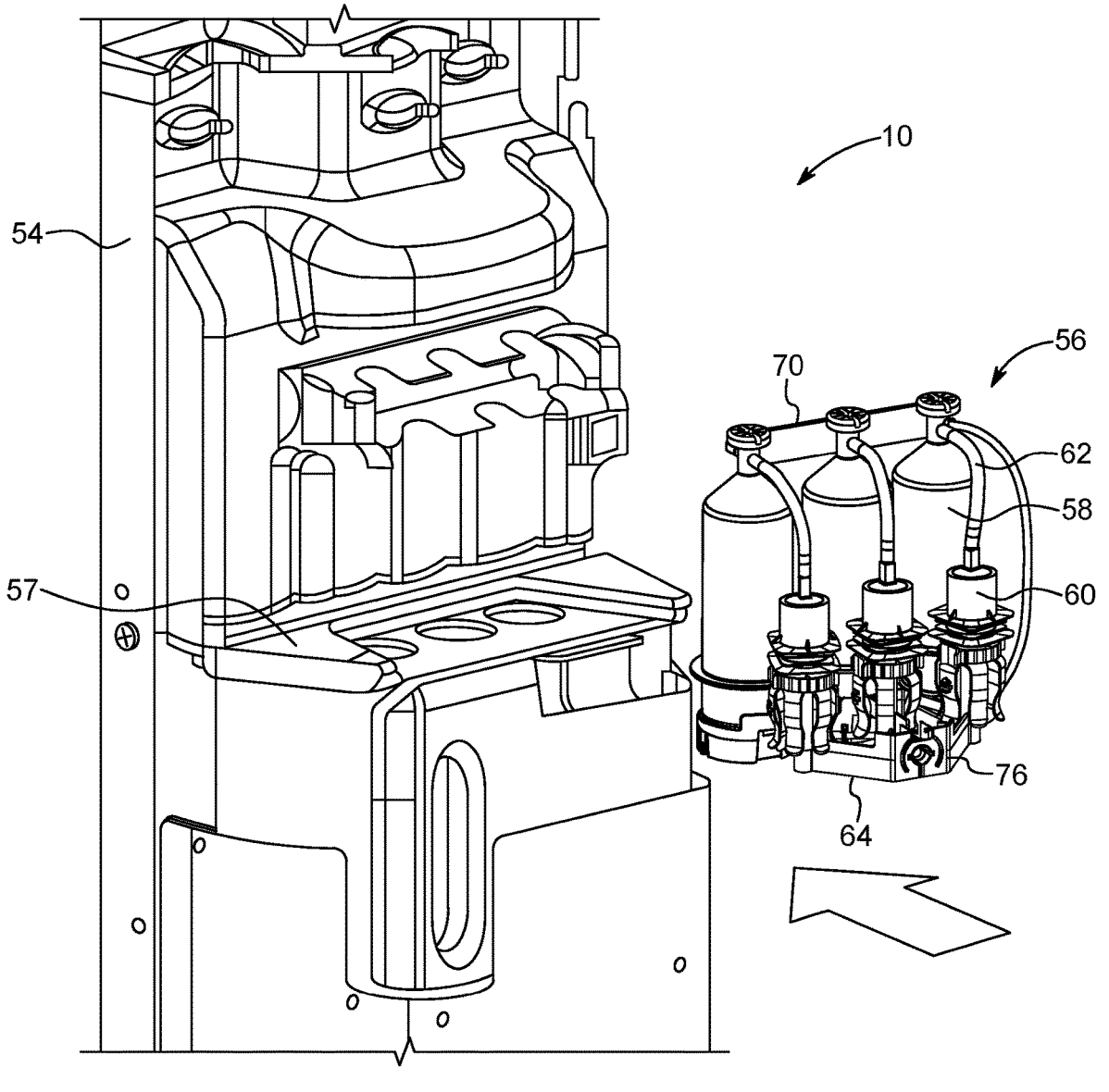
FIG. 5 is a perspective view of a fluid delivery system according to another example of the present disclosure.
Figure 6:
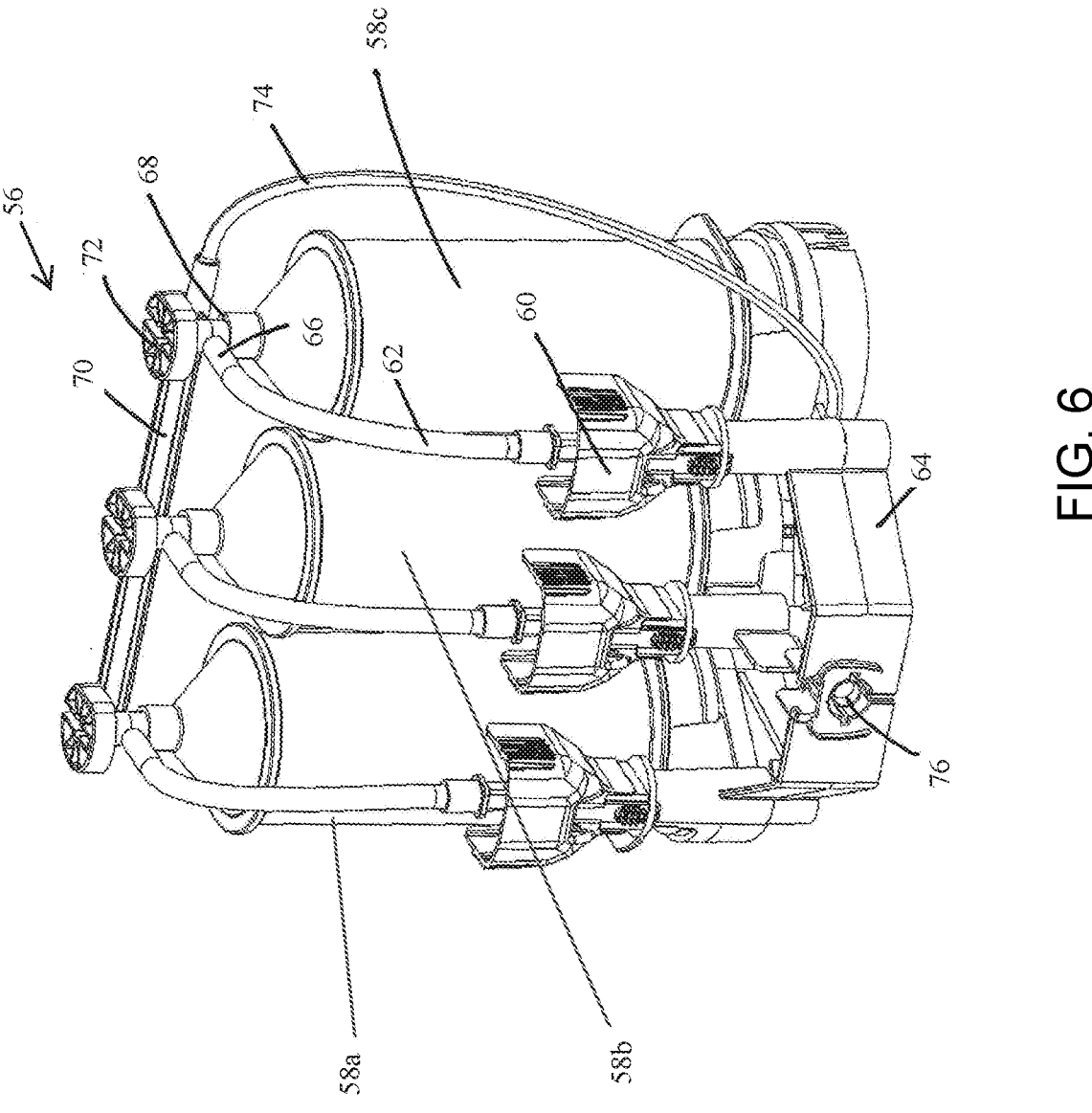
FIG. 6 is a front perspective view of a multi-use disposable system configured for use with the fluid delivery system of FIG. 5.

With reference to FIG. 5, a fluid injector 10 is shown in accordance with another example of the present disclosure. The injector 10 has a housing 54 that encloses various mechanical drive components, electrical and power components necessary to drive the mechanical drive components, and control components, such as electronic memory and electronic control devices used to control operation of reciprocally movable pistons (not shown). The fluid injector 10 further has a multi-patient disposable system (MUDS) 56 that is removably connectable with the fluid injector 10. The MUDS 56 has one or more syringes or pumps 58. In some aspects, the number of syringes 58 corresponds to the number of pistons on the fluid injector 10. In some examples, such as shown in FIG. 6, the MUDS 56 has three syringes 58a-58c in a side-by-side arrangement. Each syringe 58a-58c has a bulk fluid connector 60 for connecting to a respective bulk fluid source (not shown) via a MUDS fluid path 62. The MUDS fluid path 62 may be formed as a flexible tube with a spike element at its terminal end that connects to the bulk fluid connector 60. Injector 10 and the corresponding MUDS 56 as illustrated in FIG. 5 are described in detail in WO 2016/112163, the disclosure of which is incorporated herein by this reference.

The MUDS 56 may comprise one or more syringes or pumps 58a-58c. In some aspects, the number of syringes 58 corresponds to the number of drive members/pistons on the fluid injector 10. In some examples, such as shown in FIGS. 5 and 6, the MUDS 56 has three syringes 58a-58c arranged in a side-by-side arrangement. Each syringe 58a-58c has a bulk fluid connector 60 for connecting to a respective bulk fluid source (not shown) via a MUDS fluid path 62. The MUDS fluid path 62 may be formed as a flexible tube that connects to the bulk fluid connector 60 having a spike element at its terminal end.

With reference to FIG. 6, the MUDS 56 has a frame 64 for supporting the one or more syringes 58a-58c. The syringes 58a-58c may be removably or non-removably connected to the frame 64. Each syringe 58a-58c has an elongated, substantially cylindrical syringe body. Each syringe 58a-58c has a filling port 66 in fluid communication with the MUDS fluid path 62 for filling the syringe 58a-58c with fluid from a bulk fluid source. Each syringe 58a-58c further has a discharge outlet or conduit 68 at the terminal portion of its distal end. The discharge outlet 68 of each syringe 58a-58c is in fluid communication with a manifold 70. A valve 72 is associated with each discharge outlet 68 and is operable between a filling position, where the filling port 66 is in fluid communication with the syringe interior while the discharge outlet 68 is in fluid isolation from the syringe interior, and a delivery position, where the discharge outlet 68 is in fluid communication with the syringe interior while the filling port 66 is in fluid isolation from the syringe interior. The manifold 70 has a fluid pathway that is in fluid communication with each syringe 58a-58c and with a fluid outlet line 74 in fluid communication with a port 76 configured for connecting to a single use fluid path element (not shown) for delivering fluid to the patient.

In various embodiments, for fluid injector 10, for example any of the fluid injectors shown in FIGS. 1, 3, and 5, the motor 31 (FIG. 2) provides the motive force to reciprocally drive the drive member/piston 19 in a distal direction and discharges fluid within the syringes 12, 34 or MUDS 56. The motor 31 may have drive components, such as gears and shafts, that are operatively connected to the drive member/piston 19 to reciprocally move the drive member/piston 19. Each motor 31 must be calibrated to correlate its operating characteristics, such as input current or output torque, to a flow rate or pressure and tolerances associated therewith. As described herein, calibration may be desirable to compensate for any variations or out of specification behavior from any of the different components of the fluid injectors 10, such as any variations in motor performance characteristics, particularly in fluid injectors with two or more syringes driven by two or more motors. For example, conversion of motor input torque for one motor 31 to an injector output pressure may be different for another motor 31. This variation may be further compounded by variations in tolerances of the drivetrain of the fluid injector 10. The accuracy of flow rate or pressure in a fluid injector 10 is directly correlative to a system and method used to calibrate the motor 31.

According to one example of the present disclosure, the fluid injector 10 discussed above with respect to FIGS. 1-6 may be configured to perform a multi-phase fluid injection which includes an injection of a first fluid F1 during a first phase, followed by an injection of a second fluid F2 during a second phase. During the first phase, the first fluid F1 is injected from at least a first syringe, for example the syringe 12a of FIG. 1 or one of the syringes 58b and/or 58c of FIGS. 5-6. During the second phase, the second fluid F2 is injected from at least a second syringe, for example the syringe 12b of FIG. 1 or syringe 58a of FIGS. 5-6. Hereinafter, the first and second syringes will be discussed with reference to FIGS. 5-6, and will thus be referred to as the first syringe 58b and the second syringe 58a. However, it is to be understood that the systems and methods described herein are equally applicable to any of the syringes 12a-12b of FIG. 1, an injector with two or more rolling diaphragm syringes 34 as illustrated in FIGS. 3-4, or any other set of at least two syringes in a fluid injection system.

The first fluid F1 of the first syringe 58*b* and the second fluid F2 of the second syringe 58*a* may be different fluids, such as medical fluids having different properties, such as different viscosities. Alternatively the first fluid F1 and the second fluid F2 may be the same fluid, for example medical fluid but at different concentrations or temperatures, or the same fluid being delivered at a different flow rate. For example, the first and second fluids F1, F2 may have one or more of a different viscosity, temperature, and/or density. In one example of the present disclosure, the first fluid F1 may be contrast media, as described herein, having a first viscosity and the second fluid F2 may be saline having a second viscosity which is typically lower than the first viscosity. In certain embodiments, the fluid injector may have a third syringe 58*c*, which may contain a third fluid F3 that may be the same or different that the first fluid F1 and second fluid F2. For example, F3 may be a contrast media, which may be the same as first fluid F1 or F3 may be a different contrast agent than F1, or F3 may be the same contrast type as F1 but at a different concentration than F1. During the first phase of the multi-phase injection, the first fluid F1, i.e. contrast, may be injected from the first syringe 58*b* at a first predetermined flow rate programmed into the injector 10. Delivery of the first fluid F1 at the first predetermined flow rate is achieved by applying a pressure to the first fluid F1 in the first syringe 58*b*, such as by driving the plunger of the first syringe 58*b* with the piston 19, where the necessary applied pressure to achieve the desired first predetermined flow rate is a function of the first viscosity of the first fluid F1. Because of the generally higher viscosity of the contrast of the first fluid F1, higher applied pressures are generally required to achieve a predetermined flow rate compared to the necessary applied pressure to achieve the same flow rate for a fluid with a lower viscosity, such as saline. Following the first phase of the multi-phase injection, the second phase includes injection of the second fluid F2, i.e. saline, from the second syringe 58*a*. The second predetermined flow rate of the second fluid F2 may be the same as, greater than, or lower than the first predetermined flow rate of the first fluid F1. In fluid injections where the first and second predetermined flow rates are targeted to be the same, due to the differences between the first viscosity of the first fluid F1 and the second viscosity of the second fluid F2, the pressure required to deliver the second fluid F2 may differ from the pressure required to deliver the first fluid F1. In the present example, the pressure applied to the first fluid F1, i.e. contrast media, is generally higher than the pressure applied to the second fluid F2, i.e. saline, in order to obtain the same flow rate. In other examples, the second predetermined flow rate of the second fluid F2 may be different than the first predetermined flow rate of the first fluid F1, yet the pressures necessary to achieve the predetermined flow rates of the first fluid F1 and the second fluid F2 may still be different.

Regardless of the predetermined flow rates of the first fluid F1 and the second fluid F2, applying the pressure necessary to achieve the second predetermined flow rate of the second fluid F2 during the second phase may result in undesired fluctuations in the actual flow rate at the catheter tip of the fluid path set 17 due to the difference in the pressures applied during the first phase and the second phase of the multi-phase injection. In particular, during an initial portion of the second phase, undesirable fluctuations may occur in the actual flow rate as a result of the residual first fluid F1 in the fluid path set 17 being pushed out or purged from the fluid delivery system by the second fluid F2. Because of the residual more viscous first fluid F1 remaining in the fluid path set 17, a higher pressure may result in the less viscous second fluid F2 being ejected from the second syringe 58*b* while ejecting the residual first fluid. However, once substantially all of the residual first fluid exits the fluid path set 17, the higher pressure that is applied to the less viscous second fluid F2 may result in an undesired fluctuations in the flow rate of the second fluid F2 as it exits the catheter. The present disclosure presents methods to minimize the effect of any fluid transition, such as described herein. Additionally, in open fluid delivery systems, such as the fluid injector 10 described herein with reference to FIGS. 1-2, in which the first syringe 12*a* and the second syringe 12*b* are in fluid communication during the multi-stage injection, equalization of the capacitances of the first syringe 12*a* and the second syringe 12*b* may contribute to undesired fluctuations in the actual flow rate.

According to embodiments, in order to mitigate undesirable fluctuations in the actual flow rate, and in order to more precisely match the actual flow rate to the predetermined flow rate, an initial portion of the second phase may be a transition phase in which the pressure applied to the second fluid F2 in the second syringe 58*a* is reduced while the residual first fluid F1 is purged from the fluid delivery system.

Figure 7I:
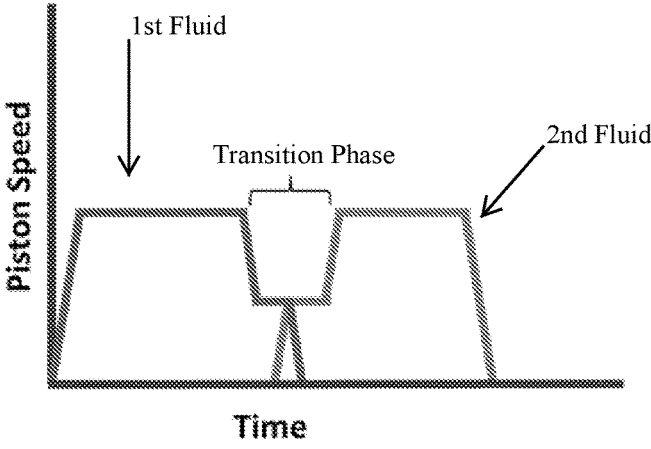

The transition phase of the multi-stage injection is performed by the electronic control devices responsible for controlling the movement of the piston 19 within the second syringe 58*a* to dispense the second fluid F2 from the second syringe 58*a*. Movement of the piston 19 is controlled via actuation of motor, such as motor 31 shown in FIG. 2, responsible for moving the piston 19 within the second syringe 58*a* to apply pressure to the second fluid F2. FIGS. 7A to 7I illustrate various non-limiting embodiments of flow rate profiles for injection of a first fluid in a first phase and a second fluid, during a transition phase and during a remaining phase utilizing the methods described herein to reduce fluid fluctuations during the transition phase. As shown in FIG. 7A, in accordance with various example of the present disclosure, the electronic control devices operate the motor 31 at a speed to inject the first fluid F1, for example from the first syringe 12*a* or 58*b* during the first phase at a first predetermined flow rate programmed into the injection 10. After injection of the first phase is completed, the electronic control devices operate the motor 31 at a lower speed (thereby reducing the pressure at which the second fluid F2 is delivered) during the transition phase, i.e. the initial portion of the second phase, to inject the second fluid F2 from the second syringe 12*b* or 58*a* to the patient at a flow rate lower than a second predetermined flow rate for the second phase. After this transition phase is completed, the electronic control devices may operate the motor 31 at a speed to inject the remaining of the second fluid F2 at the second predetermined flow rate, completing the multi-stage injection. With reference to FIG. 7B, the transition phase comprises a long ramp where injection of the second fluid ramps from a zero flow rate (zero piston speed) starting substantially concurrently with the first phase injection of the first fluid and ramps to a piston speed sufficient to provide the second predetermined flow rate after completion of the injection of the first phase. With reference to FIG. 7C, the flow profile shows an extended cross-over ramp transition phase injection protocol, where the motor speed for the first fluid phase is ramped down to zero while the motor speed of the second fluid during the transition phase is ramped up to the second predetermined flow rate. With reference to FIG. 7D, a transition phase is illustrated having a ramping transition phase that starts substantially when the motor speed of the first phase is substantially zero. FIGS. 7E and 7F illustrate a transition phases having a programmed motor speed that quickly starts at the second predetermined flow rate, then includes an optimized downward ramp when the second fluid is calculated to reach the end of the catheter, followed by a ramp back to the second predetermined phase after a the flow of the first fluid is calculated or estimated to have completed been expelled. In FIG. 7E, the transition phase ramp to the second predetermined flow rate begins prior to the end of the first phase, whereas FIG. 7F illustrates and embodiment where the transition phase ramp to the second predetermined flow rate begins after the first phase injection. With reference to FIG. 7G, a step-wise ramp of the second fluid motor speed and flow rate during the transition phase is illustrated. The step-wise ramp of motor speed may increase until the second predetermined flow rate is reached. With reference to FIG. 7H, the motor speed of the first fluid phase drive member is decreased to an intermediate speed during the transition phase and once the first motor speed reaches substantially zero, the motor speed of the second fluid phase drive member is increased to an intermediate speed during the transition phase and then is increased to a speed associated with the second predetermined flow rate. FIG. 7I, includes intermediate speed during the transition phase for both the first fluid phase and the second fluid phase, similar to FIG. 7H, having overlapping timing of the decrease and increase of the first and second injector motor, respectively, during the transition phase. The duration of the injection of the transition phase may be determined, for example, by calculating the time necessary to flow the volume of the residual first fluid F1 from the fluid path set, which may generally be calculated as the fluid volume of the fluid path set.

According to a particular example of the present disclosure, the electronic control devices are programmed to set the reduced flow rate of the transition phase in accordance with equation (2):

$$Q(t)=Q(p)-(C(1)-C(2))/t(t) \qquad (2)$$

In Equation 2, Q(t) is the reduced flow rate of the multi-phase fluid injection during the transition phase. Q(p) is the second predetermined flow rate of the injection during the second phase; C(1) is a steady state system capacitance (compliance) of the first phase determined during the injection of the first phase; C(2) is a system capacitance (compliance) of the second phase; and t(t) is a derived time for delivering the volume associated with the system compliance (C(2)). In some examples, C(2) and/or t(t) may be obtained from a lookup table or derived from an equation. In other examples, C(2) and t(t) may be obtained or derived in real time by the injector 10.

The method performed through the execution of equation (2) to calculate the reduced flow rate Q(t) during the transition phase utilizes knowledge of the system capacitance of the different phases (C(1) and C(2)) along with the transition time t(t), and the programmed flow rate of the less-viscous second phase Q(p), i.e., the predetermined flow rate. Inputs to the calculations include real-time pressure of the first fluid F1 of the first phase (P1), the derived pressure of the second fluid F2 of the second phase (P2), the derived time of transition t(t) of the transition phase, and the pre-injection volume (X2) during the second phase.

Figure 9:
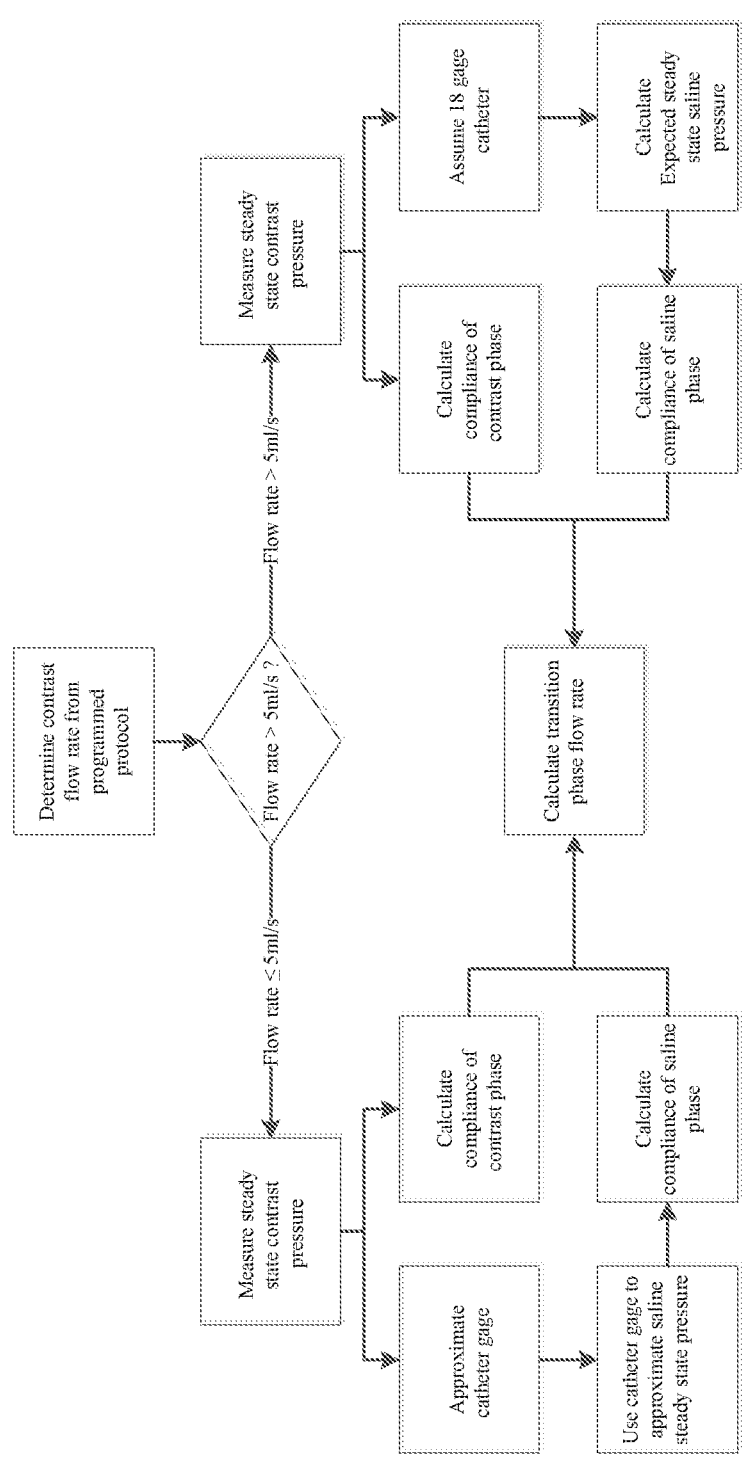
FIG. 9 is a step diagram for determining the derivation of steady state pressure for the second phase of a multi-phase fluid injection.
Figure 11:
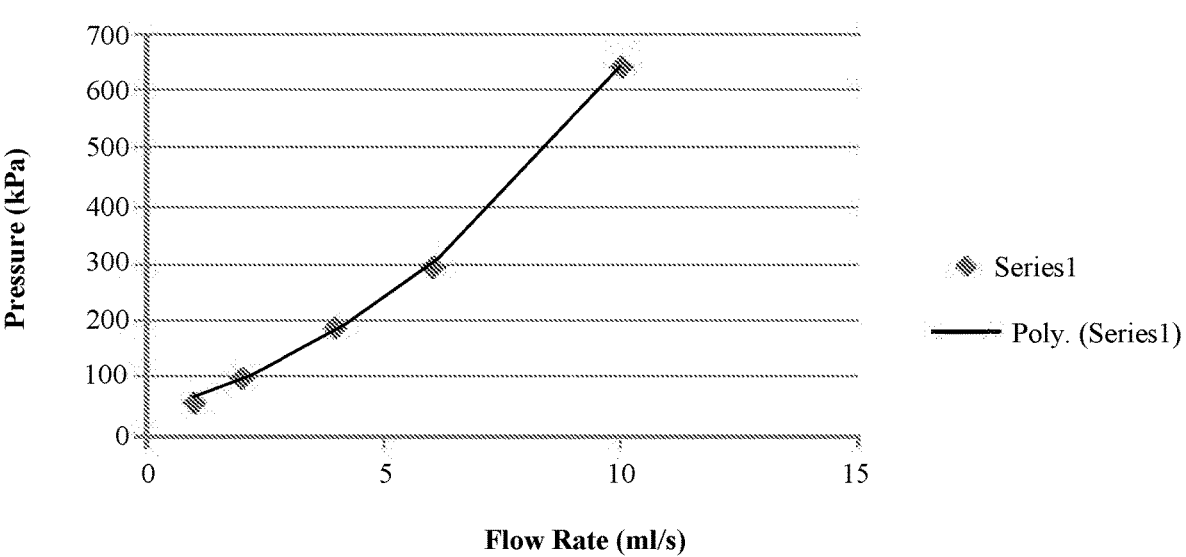
FIG. 11 is an exemplary graphed equation for deriving the steady state pressure for a multi-phase fluid injection.

The pressure of the second phase (P2) and the time of transition t(t) of the transition phase may be derived according to the step diagram of FIG. 9. In particular, the first predetermined flow rate of the first fluid F1, in this example contrast media, is used to determine how the transition phase flow rate Q(t) is calculated. If the first predetermined flow rate of the first fluid F1 is less than or equal to a threshold value, in this example 5 mL/s, the transition phase flow rate Q(t) is calculated by measuring the steady state pressure during injection of the first fluid F1, approximating the catheter gauge, and using the catheter gauge approximation to estimate the steady state pressure of the second fluid F2. In particular, the estimated steady state pressure of the second fluid F2 may be derived from the a table or other calculation based on the measured steady state pressure of the first fluid F1 as illustrated by the exemplary, non-limiting lookup table shown in FIG. 10, which provides values for system features such as rate, contrast pressure, saline pressure, and catheter size. Using the steady state pressure of the first fluid F1 and the estimated steady state pressure of the second fluid F2, respectively, the system capacitance during the first phase C(1) and the system capacitance during the second phase C(2) may be calculated as described hereinafter with particular reference to FIG. 12. The transition phase flow rate Q(t) may then be calculated from equation (2).

Where the predetermined flow rate of the first fluid F1 is greater than the threshold value, in this example 5 mL/s, the transition phase flow rate Q(t) is calculated by assuming a gauge of the catheter, calculating the estimated steady state pressure of the second fluid F2, and calculating the system capacitance during the second phase C(2). The estimated steady state pressure of the second fluid F2 may be derived from an equation such the exemplary, non-limiting equation shown in FIG. 11, showing the pressure of the second fluid F2 as a function of flow rate for a known catheter size. The system capacitance during the second phase C(2) may be calculated as described hereinafter with particular reference to FIG. 12. The transition phase flow rate Q(t) may then be calculated from equation (2).

The transition phase is timed to deliver a volume necessary to fill the fluid path set 17, which in some examples may be from 5 mL to 20 mL, depending on the tubing inner diameter and length, for example approximately 12 mL, with the second fluid F2 at the beginning of the second phase at the reduced flow rate. This allows for the residual first fluid F1 in the fluid path set to be pushed through the fluid path set 17 and the catheter at a lower flow rate and exit the fluid path set 17 and the catheter without generating undesirable fluctuations in the actual flow rate at the catheter. After the transition phase is completed, the injection of the second phase of the fluid F is returned to the predetermined programmed flow rate Q(p) of the second phase for delivery of the remaining volume of the second phase programmed by the operator.

Equation (2) may be utilized in accordance with the following steps: (1) P1 is measured during the first phase, this pressure should be measured either at a steady state or a predetermined amount of time prior to the transition to the second phase; (2) P2 is derived from a table or formula using as inputs the parameters of the second phase (i.e., second fluid F2 being used, predetermined flow rate of the second phase, catheter gauge, etc.); (3) P1 and X2 are input into the capacitance equation discussed herein to derive the volume from capacitance during the first phase; (4) P2 and X2 are input into the capacitance equation to derive the volume from capacitance during the second phase; (5) equation (1) is executed to solve for the reduced flow rate of the transition phase Q(t); and (6) the protocol is modified to deliver the transition phase at the reduced flow rate Q(t) for a volume necessary to fill the fluid path set 17, and return to the predetermined flow rate Q(p) after completion of the transition phase.

Figure 12:
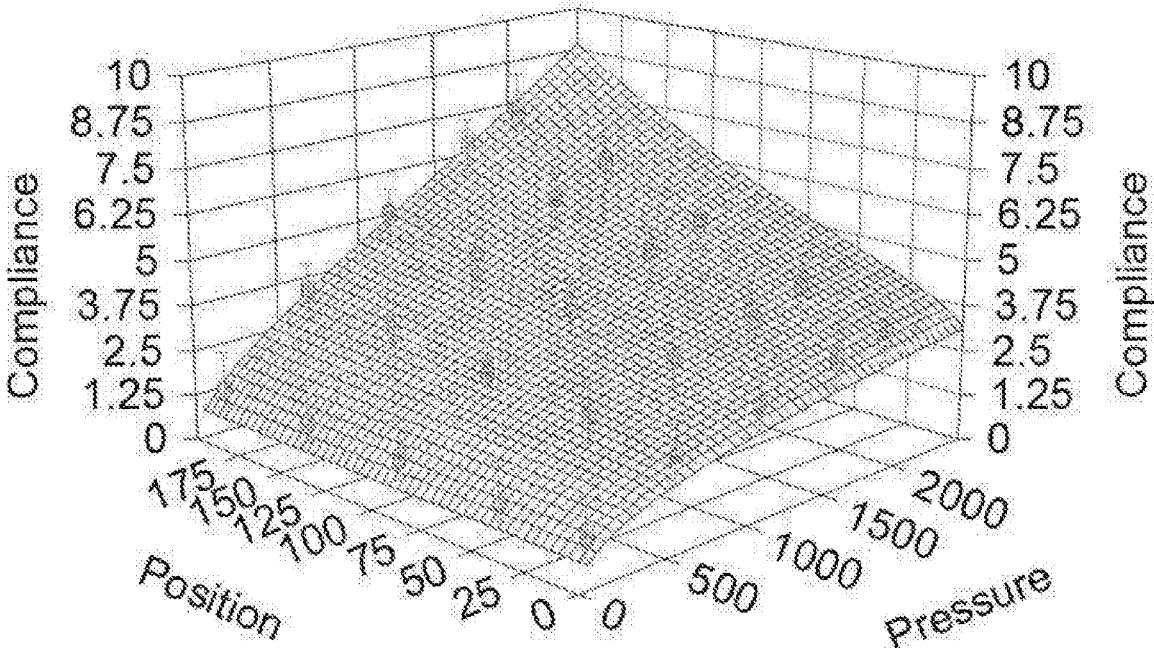
FIG. 12 is a graphical representation of a surface corresponding to a compliance equation for calculating capacitance.

According to certain embodiments, the capacitance equation may be shown graphically in FIG. 12. The capacitance properties of one exemplary fluid injector result in an under-delivery according to the following equation (3):

$$z^{-1} = a + bx^{0.5} + \frac{c}{y^{0.5}} \qquad (3)$$

wherein z is the under-delivered volume (which may be measured in any appropriate volume unit such as in milliliters ("mL")); y is the pressure (which may be measured in any appropriate pressure unit, such as in pounds per square inch ("psi")); x is the volume of fluid in the at least one syringe at the time of injection, and a, b, and c are constants for the particular surface. For example, in the surface depicted in FIG. 12, a=0.097795815, b=−0.014798654, and c=11.030418. When the under-delivered volume of fluid is determined thusly, the fluid to be injected into a patient may be corrected for and increased by the appropriate amount to compensate for the volume lost due to capacitance and impedance of the fluid injector and/or fluid. The fluid injector can overdrive the piston by the distance calculated to deliver the predicted volume that is under-delivered (i.e., z) to ensure an accurate injection dose of the fluid to the patient. The value "z" may be referred to as a "correction volume." P1 and X1 are substituted into equation (3) for y and x, respectively, to obtain the correction volume of the first phase, which is substituted for (C1) of equation (2). P2 and X2 are substituted into equation (3) for y and x, respectively, to obtain the correction volume for the second phase, which is substituted for (C2) of equation (2).

FIG. 8 is a chart illustrating the effect of utilizing the above-described transition phase on the measured flow rate of the patient catheter end of the fluid path set 17 during the transition between the first and second phases of the multi-phase fluid injection. The dashed lines represent various baseline injection flow rates, during which no transition phase was implemented. As a result, a significant increase in the measured flow rate, which correlates to a buildup of fluid pressure at the catheter, is seen at the catheter end of the fluid path set 17 during the transition from the first phase to the second phase. The solid lines represent the same flow rates as the dashed lines, but include a transition phase according to embodiments herein during an initial portion of the second phase of the multi-stage injection. As can be appreciated by a comparison of the corresponding dashed and doted lines, the implementation of a transition phase greatly reduces the measured fluctuation in flow rate at the catheter end of the fluid path set 17.

Figure 13:
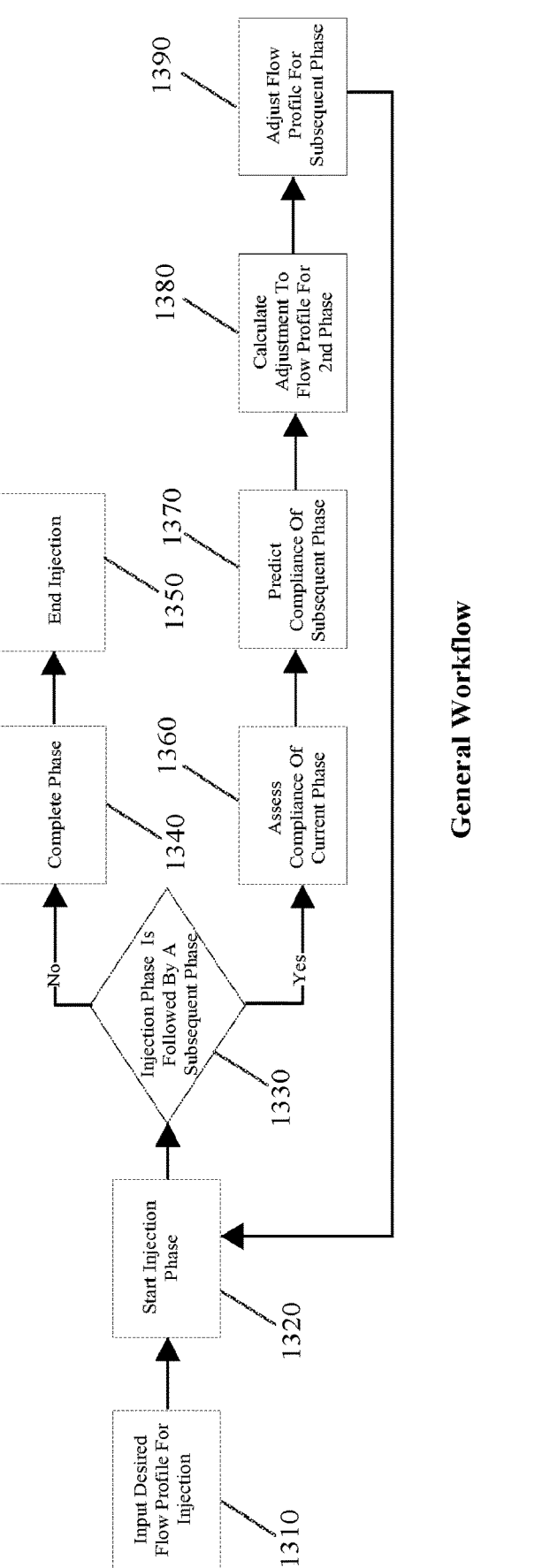
FIG. 13 illustrates a general workflow for determining the an injection protocol including a transition phase according to an embodiments.

FIG. 13 illustrates a general workflow for an injection protocol including a transition phase according to various embodiments of the present disclosure. As shown in FIG. 13, step 1310 includes input of the desired flow profile for an injection, including a first predetermined flow rate for a first fluid and in certain embodiments a second predetermined flow rate for a second fluid. The injection is started 1320 and the injector determines at step 1330 whether the first injected fluid phase is to be followed by a subsequent second injected fluid phase. If the injector processor determines that the first injected phase is not followed by a second fluid phase, the injector completes the injection of the first phase 1340 and then ends the injection 1350. Alternatively, if the injector processor determines that the first injected phase is scheduled to be followed by a second fluid phase, the injector then assesses the compliance of the currently injected first fluid phase 1360 and, based on that assessment predicts the compliance of the subsequent second fluid phase 1370, for example based on the various system components associated with the second fluid reservoir and the characteristics of the first and second fluids. Once the compliance is predicted, the fluid injector processor then calculates the appropriate adjustment to the flow rate for an initial portion of the second fluid phase injection 1380 and determines the flow rate adjustment which is used to alter the flow rate of the initial portion of the second fluid phase is to be injected. The injector then adjusts the flow profile of the initial portion of the second fluid phase 1390 to the calculated values and injects the initial portion of the second fluid at the calculated flow rate for the intermediate specified time. A feedback loop may then occur where the injector processor returns to step 1320 and starts the injection of the second fluid phase at the second predetermined flow rate after completion of the injection of the initial portion of the second fluid over the transition phase. As the protocol continues, the injector then determines if any additional phases are to be injected (i.e., subsequent contrast phases, dual flow phases, or saline phases) or if the injection protocol can be completed after injection of the second phase.

Figure 14:
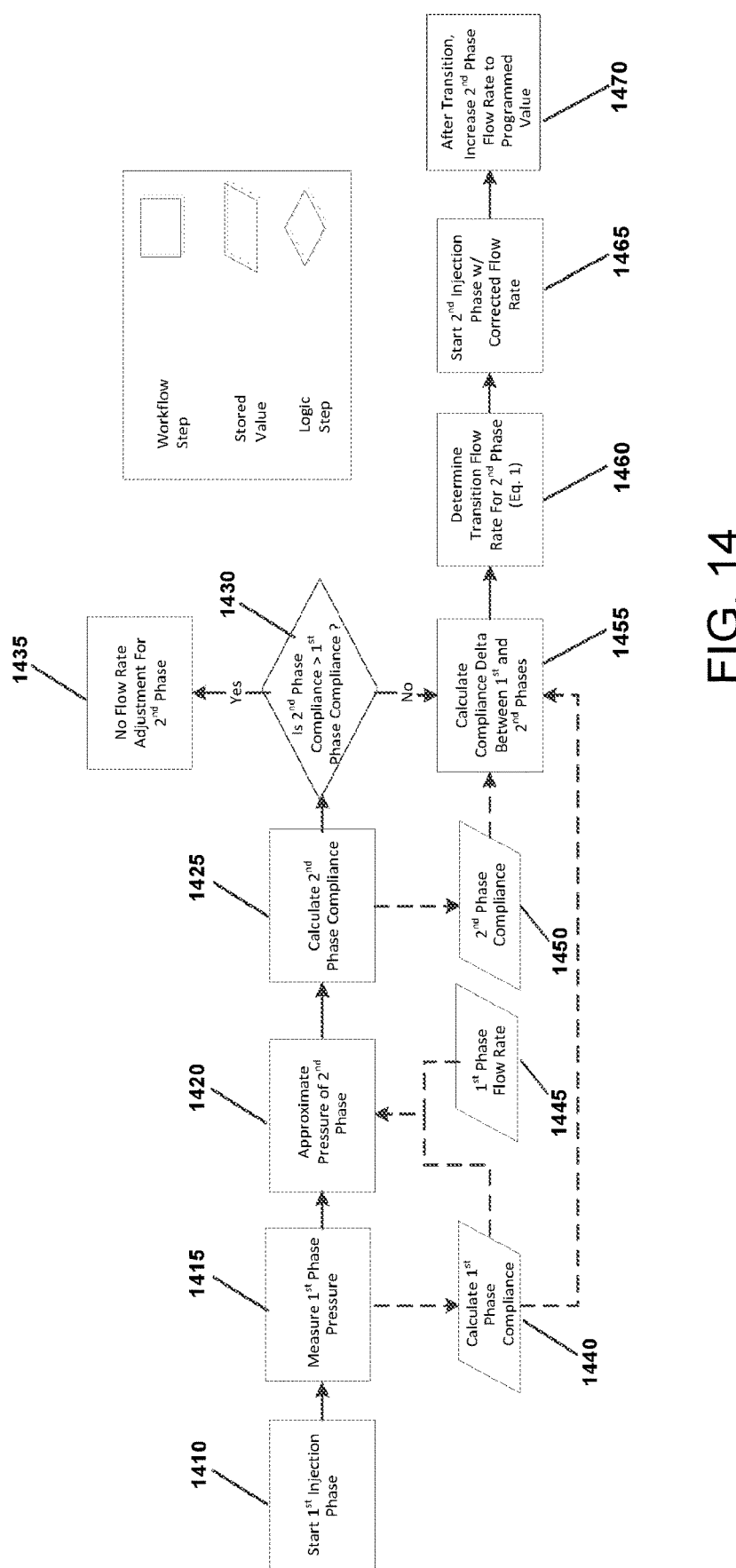
FIG. 14 illustrates a specific implementation of an injection protocol including a transition phase for an injector as illustrated in FIG. 5.

FIG. 14 illustrates a workflow for an injection protocol including a transition phase according to a specific embodiment of the present disclosure, for example the injector shown in FIG. 5. As shown in FIG. 14, step 1410 starts the first injection phase injecting the first fluid at a first predetermined pressure. The injector may measure the pressure of the first fluid in the first phase in step 1415 and calculate the compliance of the first phase 1440. Based on the measured pressure of the first fluid phase, the injector processor may approximate the pressure that the second fluid 1420 that will provide the transition phase flow rate and the second predetermined flow rate that second fluid is to be injected at, for example by reference to a data lookup table, such as shown in FIG. 11. Alternatively the injector processor may calculate the pressure that the second fluid 1420 to provide the transition phase flow rate and the second predetermined flow rate by a process as shown in FIG. 9 along with the appropriate equation or surface plot. Once the second pressure is approximated, the injector may utilize this value along with detailed information on the capacitance features of the second fluid reservoir, fluid path, and the second drive mechanism of the injector and features of the second fluid to calculate the compliance of the second fluid phase 1425. The injector processor may then determine whether the second fluid phase compliance is greater than the first fluid phase compliance in step 1430. If the second fluid phase compliance is greater than the first fluid phase compliance then the injector will determine that no flow rate adjustment is required for the initial portion of the second phase 1435 and start the injection of the second fluid phase at the second predetermined flow rate. Alternatively, if the calculations of compliance of the second fluid phase indicate there is a significant difference between the second fluid phase compliance and the first fluid phase compliance 1455, the delta between the compliance values is determined and based on the difference may be utilized to determine the intermediate flow rate for the initial portion of the second fluid phase 1460 and determine the necessary intermediate specified time period or injection volume to clear the first fluid from the fluid path/catheter, start the injection of the second fluid at the intermediate corrected flow rate 1465 and inject at the intermediate flow rate over the intermediate specified time period, and after the end of the volume delivery over the intermediate specified time period, increase the flow rate of the second fluid to the second predetermined flow rate 1470.

According to other embodiments of the workflow illustrated in FIG. 14, once the step of measuring the pressure of the first fluid phase 1415 is performed, the injector may utilize the pressure value along with detailed information on the capacitance features of the first fluid reservoir, fluid path, and the first drive mechanism of the injector and features of the first fluid to calculate the compliance of the first fluid phase 1440. The calculated compliance of the first fluid phase may be directly used to guide the approximation of the pressure in the second fluid phase 1420 and/or may be used to determine the flow rate of the first fluid phase 1445, for example to ensure that the value is substantially equal to the expected first predetermined flow rate. In other embodiments, the calculated value of the compliance of the second fluid phase 1450 and this value along with the value for the calculated compliance of the first fluid phase 1440 may be fed into step 1455 to determine the delta or difference between the calculated compliances for the first fluid phase and the second fluid phase. The described workflows are exemplary and non-limiting, as there are other workflows within the scope of the present disclosure which provide values for the first fluid and second fluid flow rates, the initial flow rate of the second fluid, the intermediate specified time for the initial flow rate of the second fluid, the compliance associated with injection of the first fluid, the compliance associated with the injection of the second fluid, and other necessary values to provide an injection protocol having a fluid transition portion that does not include any significant fluctuations in overall fluid flow.

As discussed above, after the transition phase is completed, injection of the remaining portion of the second phase is resumed at the second predetermined flow rate for the second fluid. According to an alternative example of the present disclosure, the remaining portion of the second phase is injected at a flow rate faster than the predetermined flow rate in order compensate for the effect of the slower transition phase on the total injection time for injecting both phases to the patient.

Although the disclosure has been described in detail for the purpose of illustration based on what is currently considered to be the most practical and preferred examples, it is to be understood that such detail is solely for that purpose and that the disclosure is not limited to the disclosed examples, but, on the contrary, is intended to cover modifications and equivalent arrangements. For example, it is to be understood that the present disclosure contemplates that, to the extent possible, one or more features of any example can be combined with one or more features of any other example.

The invention claimed is:

1. A fluid injector system for delivering a multi-phase fluid injection to a patient, the fluid injector system comprising:

at least one first fluid reservoir configured to contain a first fluid of the multi-phase fluid injection, the first fluid having a first viscosity;

at least one first drive member operatively connected with the at least one first fluid reservoir, the at least one first drive member being operable to dispense the first fluid of the multi-phase fluid injection;

at least one second fluid reservoir configured to contain a second fluid of the multi-phase fluid injection, the second fluid having a second viscosity different from the first viscosity;

at least one second drive member operatively connected with the at least one second fluid reservoir, the at least one second drive member being operable to dispense the second fluid of the multi-phase fluid injection;

a fluid line connected to the at least one first fluid reservoir and the at least one second fluid reservoir, and configured for delivery of at least one of the first fluid of the multi-phase fluid injection from the at least one first fluid reservoir to the patient and the second fluid of the multi-phase fluid injection from the at least one second fluid reservoir to the patient; and a control device configured to control movement of the at least one first drive member associated with the at least one first fluid reservoir and movement of the at least one second drive member associated with the at least one second fluid reservoir to control the delivery of the at least one of the first fluid and the second fluid of the multi-phase fluid injection to the patient, wherein the control device:

controls the at least one first drive member to inject the first fluid at a first predetermined flow rate during a first fluid phase, controls the at least one second drive member to inject an initial portion of the second fluid of the multi-phase fluid injection from the at least one second fluid reservoir during a transition phase at an intermediate flow rate profile different from a second predetermined flow rate for a specified intermediate time, wherein the control device calculates the intermediate flow rate profile before controlling the at least one second drive member to inject the initial portion of the second fluid, wherein the intermediate flow rate profile is calculated based on a steady state system compliance during the first fluid phase, a system compliance during a second fluid phase, and a derived time for delivering a fluid volume associated with the system compliance, wherein the specified intermediate time is selected to allow a residual portion of the first fluid to pass through the fluid line to the patient so that the residual portion of the first fluid is purged from the fluid line by an end of the specified intermediate time before beginning to inject a remaining portion of the second fluid, and wherein the specified intermediate time is based on a system architecture, a capacitance of at least one of the at least one first fluid reservoir, the at least one second fluid reservoir, a length of the fluid line, a diameter of the fluid line, a volume of the fluid line, a length of a catheter, a diameter of the catheter, a volume of the catheter, and any combination thereof, wherein a volume of the initial portion of the second fluid of the multi-phase fluid injection is determined by one or more of a volume capacity of the fluid line between the at least one second fluid reservoir and the patient, the capacitance of at least one of the at least one first fluid reservoir and the at least one second fluid reservoir, and injector system compliance, wherein the at least one first fluid reservoir is selected from the group consisting of a first syringe, a first peristaltic pump, and a first compressible bag, and wherein the at least one second fluid reservoir is selected from the group consisting of a second syringe, a second peristaltic pump, and a second compressible bag, and injects the remaining portion of the second fluid of the multi-phase fluid injection at a flow rate at least equal to the second predetermined flow rate directly after the injection of the initial portion of the second fluid.

2. The fluid injector system of claim 1, wherein the first viscosity is greater than the second viscosity.

3. The fluid injector system of claim 1, wherein the intermediate flow rate profile of at least the initial portion of the second fluid is delivered at a flow rate lower than the first predetermined flow rate.

4. The fluid injector system of claim 1, wherein the first fluid is selected from the group consisting of a contrast media, and a mixture of a first specific ratio of the contrast media and saline, and wherein the second fluid is selected from the group consisting of saline and a mixture of a second specific ratio of the contrast media and saline.

5. The fluid injector system of claim 1, wherein the intermediate flow rate profile of the initial portion is calculated based on the following equation:

$$Q(\text{transition}) = Q(\text{programmed}) - Q(\text{adjusted})$$

wherein Q(transition) is a desired flow rate profile at a transition between the first fluid and at least the second fluid; Q(programmed) is a desired flow rate profile for the first fluid and at least the second fluid; and Q(adjusted) is a necessary adjustment of a flow rate of the second fluid so that Q(transition) at the transition between the first fluid and at least the second fluid results in a flow rate at a catheter tip that is substantially similar to Q(programmed).

6. The fluid injector system of claim 1, wherein the intermediate flow rate profile of the initial portion of the second fluid is calculated based on the following equation:

$$Q(t) = Q(p) - (C(1) - C(2))/t(t),$$

wherein Q(t) is the intermediate flow rate profile, Q(p) is the second predetermined flow rate, C(1) is the steady state system compliance during the first fluid phase, C(2) is the system compliance during injection of the second fluid, and t(t) is the derived time for delivering the fluid volume associated with the system compliance (C(2)).

7. The fluid injector system of claim 1, wherein the intermediate flow rate profile of at least the initial portion of the second fluid is delivered at a flow rate that varies between zero and the second predetermined flow rate over the specified intermediate time.

\* \* \* \* \*